(12) United States Patent  
Tada

(10) Patent No.: US 8,374,803 B2
(45) Date of Patent: Feb. 12, 2013

(54) DAMAGE DETECTION APPARATUS, DAMAGE DETECTION METHOD AND RECORDING MEDIUM

(75) Inventor: Naoya Tada, Okayama (JP)

(73) Assignee: National University Corporation Okayama University, Okayama-Shi (JP)

( * ) Notice: Subject to any disclaimer, the term of this patent is extended or adjusted under 35 U.S.C. 154(b) by 626 days.

(21) Appl. No.: 12/223,063

(22) PCT Filed: Jan. 31, 2007

(86) PCT No.: PCT/JP2007/051647
§ 371 (c)(1),
(2), (4) Date: Jul. 22, 2008

(87) PCT Pub. No.: WO2007/088913
PCT Pub. Date: Aug. 9, 2007

(65) Prior Publication Data
US 2009/0192730 A1    Jul. 30, 2009

(30) Foreign Application Priority Data
Jan. 31, 2006  (JP) .................... 2006-023447

(51) Int. Cl.
*G01B 5/28* (2006.01)
(52) U.S. Cl. ............. 702/38; 702/34; 702/35; 702/36; 702/155; 702/168; 702/170; 702/64
(58) Field of Classification Search ............ 702/38
See application file for complete search history.

(56) References Cited

U.S. PATENT DOCUMENTS 4,764,970 A * 8/1988 Hayashi et al. ............ 382/149
4,914,378 A * 4/1990 Hayashi et al. ............ 324/696

FOREIGN PATENT DOCUMENTS

| JP | A-61-292546 | 12/1986 |
| JP | A-64-035357 | 2/1989 |
| JP | A-01-110248 | 4/1989 |
| JP | A-06-109684 | 4/1994 |
| JP | A-07-116142 | 5/1995 |

OTHER PUBLICATIONS

Soboyejo, "A study of the interaction and coalescence of two coplanar fatigue cracks in bending," Fatigue Fract. Eng. Mater. Struct, (1989) (hereinafter Soboyejo).*

(Continued)

*Primary Examiner* — Jonathan C Teixeira Moffat
*Assistant Examiner* — Hyun Park
(74) *Attorney, Agent, or Firm* — Oliff & Berridge, PLC

(57) ABSTRACT

A damage detection apparatus and method which detect a damage occurring in a specimen include energizing an inspection area on a specimen into a predetermined energized condition, measuring a potential difference at predetermined intervals in the inspection area, and analyzing an existence or otherwise of a damage, and a shape thereof, based on a plurality of items of potential difference data. Parameters specifying a hypothetical damage are hypothesized in advance and, based on the potential difference data, calculation is executed using a maximum likelihood estimation method on a double body in which hypothetical specimens are doubled by bringing together their front surfaces, and furthermore on a quadruple body quadrupled by bringing rear surfaces of hypothetical specimens together, a maximum likelihood estimation value of the parameters is calculated.

5 Claims, 18 Drawing Sheets

OTHER PUBLICATIONS

Scott et al., Maximum Likelihood Estimation, edited by Silverman (2004), cnx.org.*

Toda, "Three dimensional identification of semi-elliptical surface crack by means of direct-current electrical potential difference method with multiple probe sensor," PVP vol. 471 Fitness for Service, Life Extension, Remediation, Repair and Erosion/Corrosion Issue for Pressure Vessel Componens (2004).*

Tada; "Potential Difference Method for Non-Destructive Evaluation of Defects and Materials;" *Journal of JSNDI*; May 1, 2002; pp. 258-264; vol. 51; No. 5; Japan.

Iwamoto; "Experimental Study of Identification of a Semi-Elliptical Surface Crack by DC-PDM with Multiple-Type Probe;" *The Japan Society of Mechanical Engineers 2003 Nendo Nenji Taikai Koen Ronbunshu*; Aug. 8, 2003; pp. 223-224; No. 03-1; Japan.

* cited by examiner

US 8,374,803 B2

DAMAGE DETECTION APPARATUS, DAMAGE DETECTION METHOD AND RECORDING MEDIUM

TECHNICAL FIELD

The present invention relating to a damage detection apparatus, a damage detection method, and a recording medium on which is recorded a damage detection program, in particular, it relates to a damage detection apparatus, a damage detection method, and a recording medium on which is records a damage detection program, which measure a potential difference in a necessary area, while sending a direct current through a specimen which is a subject of inspection, and detect a damage such as a crack or a wastage occurring in the specimen using the potential difference data.

BACKGROUND ART

To date, an inspection technique using a direct current potential difference method which measures a potential difference distribution on a specimen surface while sending a direct current through the specimen, which is an inspection subject structure, and indirectly detects a damage, such as an existence or otherwise of a crack in the specimen and a condition of the crack, from the potential difference distribution, has been known as one nondestructive inspection technique.

Recently, a nondestructive inspection method has also been proposed which, using the direct current potential difference method, enables a quantification of a damage such as a crack buried inside a specimen, or a crack exposed on a surface, as a three-dimensionally shaped damage having an optional aspect ratio and inclination.

That is, by first sending a predetermined current through the specimen and acquiring potential difference values at predetermined positions, and next, using analysis means such as a finite element method, setting a shape of a damage such as a hypothetical crack, which is to be a subject of detection, and carrying out a calculation based on the acquired potential difference values, the method identifies a shape of the damage (for example, refer to Patent Document 1 and Patent Document 2).

Patent Document 1: JP-A-64-035357
Patent Document 2: JP-A-06-109684

DISCLOSURE OF THE INVENTION

Problems the Invention is to Solve

However, as a calculation with heretofore known calculation methods, such as this kind of finite element method, necessitates a large amount of time, it has been practically impossible to calculate a shape as an initial value of a damage changed in various ways.

Although there is also a method which achieves an increase in a capacity of a calculator itself as a method of increasing a calculation speed, in the case of increasing the capacity of the calculator itself, a cost of the calculator has increased, and it has been impractical.

The inventor, bearing in mind this kind of current situation, has carried out research in order to develop a calculation method which calculates more simply, resulting in the contrivance of the invention.

Means for Solving the Problems

The damage detection apparatus of the invention, being a damage detection apparatus which detects a damage occurring in a specimen, which is a subject of detection, includes: energizing means which energizes in order to put an inspection area on the specimen into a predetermined energized condition; potential difference measurement means which measures a potential difference at predetermined intervals in the inspection area; storage means which stores a plurality of items of potential difference data acquired with the potential difference measurement means; and analysis means which determines an existence or otherwise of a damage, and a shape thereof, based on the potential difference data stored in the storage means. The analysis means sets parameters specifying a hypothetical damage, sets hypothetical specimens having the hypothetical damage and, as well as doubling them by bringing together front surfaces of the hypothetical specimens, sets a quadruple body, quadrupled by bringing rear surfaces of the hypothetical specimens together with each rear surface of the doubled hypothetical specimen, and executes a calculation, based on the potential difference data, using a maximum likelihood estimation method, calculating a maximum likelihood estimation value of the parameters for the quadruple body, and detecting a damage.

Furthermore, the damage detection apparatus of the invention is also characterized by the following points. That is, (1) in the event that the damage is a crack formed in the specimen, when setting the quadruple body having the hypothetical damage, making the hypothetical damage an elliptical crack, (2) in the event that the damage is a wall thinning of the specimen, making a parameter specifying the hypothetical damage a thickness of the specimen, and calculating an amount of wall thinning from a thickness of the specimen calculated by a calculation using the maximum likelihood estimation method.

Also, the damage detection method of the invention, being a damage detection method which detects a damage occurring in a specimen, which is a subject of detection, includes: a step of, while carrying out a predetermined energizing in an inspection area on the specimen, measuring a plurality of potential differences at predetermined intervals in the inspection area; a step of setting parameters specifying a hypothetical damage; a step of setting hypothetical specimens having the hypothetical damage and, as well as doubling them by bringing together front surfaces of the hypothetical specimens, setting a quadruple body, quadrupled by bringing rear surfaces of the hypothetical specimens together with each rear surface of the doubled hypothetical specimen, executing a calculation, based on the potential difference data, using a maximum likelihood estimation method, and calculating a maximum likelihood estimation value of the parameters for the quadruple body; and a step of detecting an existence or otherwise of a damage and/or a shape thereof from the maximum likelihood estimation value.

Also, the recording medium of the invention, on which is recorded a damage detection program, is a computer readable recording medium on which is recorded a damage detection program for causing a computer to execute: a step of, while carrying out a predetermined energizing in an inspection area on the specimen, measuring a plurality of potential differences at predetermined intervals in the inspection area; a step of setting parameters specifying a hypothetical damage; a step of setting hypothetical specimens having the hypothetical damage and, as well as doubling them by bringing together front surfaces of the hypothetical specimens, setting a quadruple body, quadrupled by bringing rear surfaces of the hypothetical specimens together with each rear surface of the doubled hypothetical specimen, executing a calculation, based on the potential difference data, using a maximum likelihood estimation method, and calculating a maximum likelihood estimation value of the parameters for the quadruple body; and a step of detecting an existence or otherwise of a damage and/or a shape thereof from the maximum likelihood estimation value.

Advantage of the Invention

With the damage detection apparatus and damage detection method of the invention, it being a damage detection apparatus which, by setting parameters specifying a hypothetical damage in a specimen, which is a subject of detection, executing a calculation using the maximum likelihood estimation method, using potential difference data measured in an inspection area, and calculating a maximum likelihood estimation value of the parameters, identifies values of the parameters and detects a damage, as it is possible by, when executing the calculation using the maximum likelihood estimation method, as well as doubling the hypothetical specimens by bringing together front surfaces thereof, setting a quadruple body, quadrupled by bringing rear surfaces of the hypothetical specimens together with each rear surface of the doubled hypothetical specimen, and executing a calculation on the quadruple body using the maximum likelihood estimation method, to simplify the calculation using the maximum likelihood estimation method by utilizing a symmetry in the quadruple body, it is possible to determine an existence or otherwise of damage, and a shape thereof, in an extremely short time.

In particular, with the analysis means which executes a calculation using the maximum likelihood estimation method, in the event that the damage is a crack, by setting an elliptical crack as the hypothetical damage when setting the quadruple body having the hypothetical damage, it being possible to greatly reduce a process time with the analysis means, it is possible to determine an existence or otherwise of the damage, and a shape thereof, instantaneously.

Also, with the analysis means, in a case of the damage being a wall thinning of the specimen, by making a parameter specifying the hypothetical damage a thickness of the specimen, and obtaining an amount of wall thinning from a thickness of the specimen obtained by a calculation using the maximum likelihood estimation method, it is possible to greatly reduce a process time with the analysis means.

BRIEF DESCRIPTION OF THE DRAWINGS

FIG. 5A is an illustration of a model of a specimen having a crack, while

FIG. 6A is an illustration of a model of a double body having a crack, while

FIG. 7A is an illustration of a model of a quadruple body having a crack, while

FIG. 8A is an illustration of a model of a specimen having a crack, while

DESCRIPTION OF REFERENCE NUMERALS AND SIGNS

Figure 1:
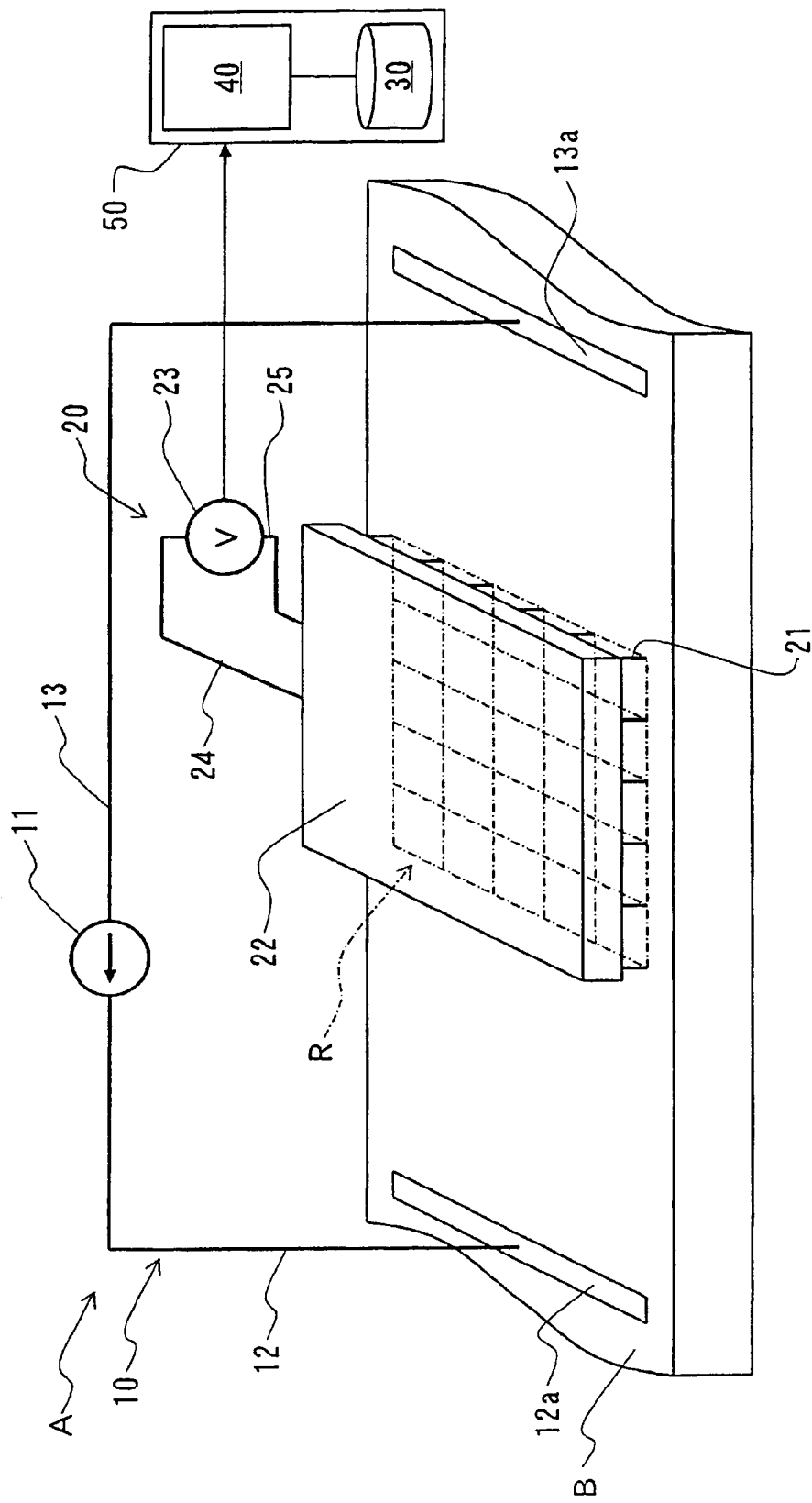
FIG. 1 is a block diagram showing a configuration of a damage detection apparatus of an embodiment.

A Damage detection apparatus
B Specimen
R Inspection area
10 Energizing section
11 Direct current power source
12 Current input wire
13 Current output wire
20 Potential difference measurement section
21 Probe
22 Probe support
23 Voltmeter
24 First wiring
25 Second wiring
40 Analysis section

BEST MODE FOR CARRYING OUT THE INVENTION

With a damage detection apparatus and a damage detection method of the present invention, in a case of identifying by analysis damage occurring in a specimen which is a subject of inspection, an identification is done by carrying out a calculation using a maximum likelihood estimation method. Consequently, it is possible to reduce a burden on the calculation in the analysis, and to accelerate a calculation process.

Moreover, in a case of executing a calculation using the maximum likelihood estimation method, as well as setting parameters specifying a hypothetical damage, setting hypothetical specimens having the hypothetical damage, and doubling them by bringing together front surfaces of the hypothetical specimens, a quadruple body, quadrupled by bringing rear surfaces of the hypothetical specimens together with each rear surface of the doubled hypothetical specimen, is set, and a maximum likelihood estimation value of parameters is obtained for the quadruple body by executing a calculation using the maximum likelihood estimation method, based on potential difference data.

Consequently, as it is possible, when executing the calculation using the maximum likelihood estimation method, to greatly reduce an actual amount of calculation by utilizing a symmetry of the quadruple body, it being possible to obtain the maximum likelihood estimation value of the parameters in an extremely short time, it is possible to identify damage occurring in the specimen in an extremely short time.

In particular, in a case of the damage being a crack, with analysis means, by setting an elliptical crack as the hypothetical damage when simulating the quadruple body having the hypothetical damage, it being possible to greatly reduce a process time with the analysis means, it is possible to determine an existence or otherwise of the damage, and a shape thereof, instantaneously.

Also, in a case of the damage being a wall thinning of the specimen, by making a parameter specifying the hypothetical damage a thickness of the specimen, and obtaining an amount of wall thinning from a thickness of the specimen obtained by a calculation using the maximum likelihood estimation method, it being possible to greatly reduce a process time with the analysis means, it is possible to determine the amount of wall thinning instantaneously.

Hereafter, a description will be given, based on the drawings, of an embodiment of the invention. FIG. 1 is an outline schematic diagram of a damage detection apparatus A of the embodiment.

The damage detection apparatus A of the embodiment includes an energizing section 10, consisting of energizing means which sends a predetermined current through an inspection area R of a specimen B, a potential difference measurement section 20, consisting of potential difference measurement means which measures a potential difference in the inspection area R at predetermined intervals, a storage section 30, consisting of storage means which stores a plurality of items of potential difference data acquired by the potential difference measurement section 20, and an analysis section 40, consisting of analysis means which, based on the potential difference data stored in the storage section 30, determines an existence or otherwise of damage and/or a shape of the damage.

Herein, the specimen B of the embodiment is taken to be a pipe of a metal having a conductive property, such as stainless steel.

The energizing section 10 is configured of a direct current power source 11, which enables an output of a required direct current, and a current input wire 12 and current output wire 13, one extremity of each of which is connected to the direct current power source 11.

Highly conductive connection pads 12a and 13a being provided respectively at the other extremities of the current input wire 12 and current output wire 13, by positioning the inspection area R of the specimen B between the connection pads 12a and 13a, the inspection area R is energized as evenly as possible. In particular, disposing the connection pads 12a and 13a as far away from each other as possible, an approximately even current is sent through the inspection area R.

The potential difference measurement section 20 is configured of a probe support 22, from which protrude a plurality of probes 21, and a voltmeter 23, which detects a potential difference between any two probes 21 and 21 on the probe support 22.

In the embodiment, the plurality of probes 21 being disposed in a matrix form at predetermined intervals on the probe support 22, each probe 21 and the voltmeter 23 are connected via a switching circuit (not shown), connected to the voltmeter 23, which switches between the probes 21. In FIG. 1, 24 being a first wiring connecting the probe support 22 and the voltmeter 23, 25 is a second wiring connecting the probe support 22 and the voltmeter 23. Although not shown in the figure, a control signal wire for inputting a control signal for controlling the switching circuit is connected to the probe support 22.

It is also acceptable, rather than carrying out a measurement while switching between the probes 21 connected to the voltmeter 23 by the switching circuit, to arrange in such a way as to, while appropriately moving two probes 21 and 21, each of which is connected to the voltmeter 23, measure a potential difference between the probes 21 and 21 in a predetermined position.

The storage section 30 and analysis section 40 are, in the embodiment, configured of a personal computer 50. That is, the storage section 30 being configured of a storage device, such as a hard disc or a memory, in the personal computer 50, the analysis section 40 executes an analysis, to be described hereafter, by loading an analysis program stored on the hard disc, and executing a predetermined process with a CPU.

Figure 2:
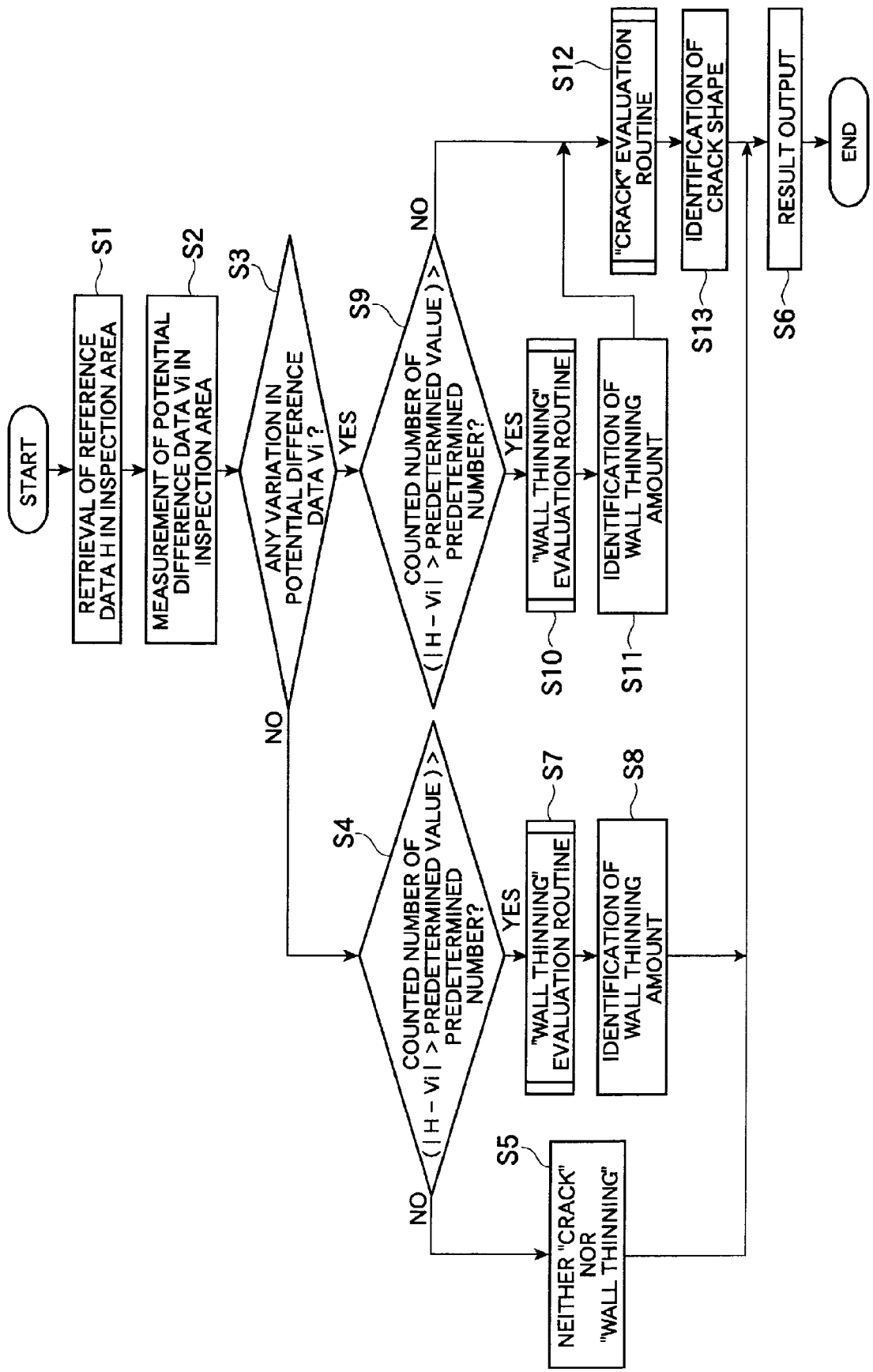
FIG. 2 is a flowchart showing a flow of a process in the damage detection apparatus of the embodiment.

With the analysis program of the embodiment, an analysis is executed based on the flowchart shown in FIG. 2.

Firstly, in the analysis section 40, based on the analysis program, reference data H of the inspection area R, stored in advance in the storage section 30 consisting of the storage device such as the hard disc or the memory, is retrieved (step S1).

The reference data H being an inspection area R potential difference measurement result measured by the damage detection apparatus A at an initial stage of manufacture, as it is a result of measuring the potential difference in a condition, at the initial stage of manufacture, in which it can be supposed that no damage exists, stored in the storage section 30, it is used for determining an existence or otherwise of "wall thinning", in a way to be described hereafter.

Herein, in the embodiment, the specimen B of the inspection area R is taken to have a uniform thickness. Furthermore, a uniform current being sent through the inspection area R in a predetermined direction by the energizing section 10, a detection of a potential difference by the potential difference measurement section 20, as well as being carried out by probes 21 separated at predetermined intervals in the energizing direction, is carried out by probes 21 separated at predetermined intervals in a direction perpendicular to the energizing direction.

As the specimen B of the inspection area R is taken to have a uniform thickness, the inspection area R is approximately equipotential in the direction perpendicular to the energizing direction. Consequently, in the inspection area R, a potential difference measured in the direction perpendicular to the energizing direction is approximately "zero".

Therein, in a case in which the intervals between the probes 21 aligned in the matrix form are made equal intervals, it is possible to make the reference data H an average value of results of measuring a potential difference in each probe 21 interval in the energizing direction in the inspection area R. In the embodiment, as the intervals between the probes 21 are made equal intervals, the average value of the results of measuring the potential difference in each probe 21 interval in the energizing direction in the inspection area R is made the reference data H. Alternatively, it is also possible to use a logical value acquired by a calculation as the reference data H.

Next, in the analysis section 40, based on the analysis program, the inspection area R is put into a predetermined energized condition with the energizing section 10, potential difference data Vi between predetermined probes 21 in the inspection area R are taken with the potential difference measurement section 20, and each item of potential difference data Vi, which are the acquired measurement results, is stored in the storage section 30 (step S2). One item of potential difference data Vi exists for each measurement point set by the potential difference measurement section 20 in the inspection area R.

Herein, the uniform current being sent through the inspection area R in the predetermined direction by the energizing section 10, the detection of the potential difference by the potential difference measurement section 20, as well as being carried out by the probes 21 separated at the predetermined intervals in the energizing direction, is carried out by the probes 21 separated at the predetermined intervals in the direction perpendicular to the energizing direction. The intervals between the probes 21 when measuring are taken to be constant.

In a case in which a "crack" exists in the inspection area R, the potential difference data Vi show a large value in a vicinity of the "crack", in a case in which a "wall thinning" occurs in the inspection area R, a uniform increase from the reference data H is observed in the potential difference data Vi in the energizing direction in the inspection area R, and in a case in which a "crack" and a "wall thinning" exist in the inspection area R, as well as a uniform increase from the reference data H being observed in the potential difference data Vi in the energizing direction in the inspection area R, the potential difference data Vi in a vicinity of the "crack" show an extremely large value.

Therein, in the analysis section 40, firstly, an existence or otherwise of a variation in the measurement result potential difference data Vi stored in the storage section 30 is determined, and a determination of an existence or otherwise of a "crack" in the inspection area R is carried out (step S3) That is, in the event that no "crack" exists in the inspection area R, the potential difference data Vi in the energizing direction are uniform potential difference data Vi with no variation, while in the event that there is a variation in the potential difference data Vi, it can be determined that there is a "crack".

Herein, it is acceptable either that the determination of the existence or otherwise of a variation is carried out based on a standard deviation value of the potential difference data Vi, or that it is carried out by counting a number of items of potential difference data Vi which exceed a threshold value set in advance.

In the event that there is no variation in the potential difference data Vi, in the analysis section 40, it is determined whether a difference between the potential difference data Vi in the energizing direction and the reference data H is equal to or greater than a predetermined value, and a determination of an existence or otherwise of a "wall thinning" is carried out (step S4).

That is, in step S4, in the analysis section 40, the difference between the potential difference data Vi in the energizing direction and the reference data H is calculated, a number of items of potential difference data Vi whose difference values exceed a predetermined threshold value is counted and, in the event that the number counted is within a predetermined number, in the analysis section 40, it is determined that there is neither a "crack" nor a "wall thinning" in the inspection area R (step S5), and a "no problem" result is output (step S6).

Meanwhile, in step S4, in the event that the number of items of potential difference data Vi whose difference values exceed the predetermined threshold value exceeds the predetermined number, in the analysis section 40, it is determined that a "wall thinning" exists in the inspection area R, a "wall thinning" evaluation routine is executed (step S7), and an amount of wall thinning is identified.

In the embodiment, in step S4, although the number of items of potential difference data Vi for which the value of the difference between the potential difference data Vi in the energizing direction and the reference data H exceeds the predetermined threshold value is counted, it is also acceptable to calculate an average value h of the potential difference data Vi in the energizing direction, and determine the existence or otherwise of a "wall thinning" depending on whether or not a difference between the average value h and the reference data H exceeds a predetermined threshold value.

That is, in the case of step S4, there being no effect of a "crack" on the potential difference data Vi, it is only possible for an increase in the potential difference due to a "wall thinning" to occur in the potential difference data Vi so, a comparison being possible between the average value h of the potential difference data Vi in the energizing direction and the reference data H, it is possible to swiftly execute a comparison determination in step S4 by using the average value h of the potential difference data Vi in the energizing direction.

In the "wall thinning" evaluation routine executed in step S7, it is presumed that a uniform wall thinning is occurring in the inspection area R, and the evaluation of the amount of wall thinning is carried out using a hypothetical damage parameter t which represents a thickness of the specimen B.

Herein, as a dimension of the intervals between the probes 21 which take the potential difference data Vi, a resistivity of the specimen B, and a current value of a current sent through the inspection area R by the energizing section 10, are all known invariables, it is possible, in a case of a direction parallel to the energizing direction, to evaluate a voltage value in a portion between the probes 21 corresponding to the potential difference data Vi as a product of an inverse of the parameter t and a required invariable G. In a case of the direction perpendicular to the energizing direction, the voltage value in the portion between the probes 21 corresponding to the potential difference data Vi is "0". Also, in a case in which the dimension of the intervals between the probes 21 is not constant, it is also acceptable to normalize at a dimension di of the intervals between the probes 21 in a case of being predetermined potential difference data Vi.

A value of the invariable G being decided from a value of the dimension of the intervals between the probes 21, a value of the resistivity of the specimen B, and the current value of the current sent through the inspection area R by the energizing section 10, by obtaining a value of the parameter t at which a logical value "G/t" of the potential difference data Vi in the energizing direction, and the average value h of the potential difference data Vi in the energizing direction, coincide, the value of the parameter t is identified in the analysis section 40.

Then, in the analysis section 40, the amount of wall thinning is identified from a difference between the acquired value of the parameter t of the specimen B and an original thickness dimension of the specimen B (step S8). Subsequently, in the analysis section 40, the amount of wall thinning identified in step S8 is output in step S6.

In step S3, in the case in which there is a variation in the potential difference data Vi, in the analysis section 40, the determination of the existence or otherwise of a "wall thinning" is carried out by counting the number of items of potential difference data Vi for which the difference between the reference data H and the potential difference data Vi is equal to or greater than a predetermined threshold value, and determining whether the number counted is greater than a predetermined number (step S9).

That is, in step S3, in the case in which there is a variation in the potential difference data Vi, although there is a possibility that the potential difference data Vi are being affected by two kinds of damage, a "wall thinning" and a "crack", as the potential difference data Vi in the energizing direction increase uniformly from the reference data H in the event that a "wall thinning" exists, as opposed to the potential difference data Vi increasing locally in the event of a "crack" existing, it is possible to count the number of items of potential difference data Vi for which the difference between the reference data H and the potential difference data Vi is equal to or greater than the predetermined threshold value, and determine that a "wall thinning" exists in the event that the number counted is greater than the predetermined number.

In step S9, in the event that it is determined that a "wall thinning" exists in the inspection area R, the analysis section 40 executes a "wall thinning" evaluation routine (step S10), identifying the amount of wall thinning.

Herein, as there is a possibility that the potential difference data Vi are being affected by damage due to a "crack", in the event that the "wall thinning" evaluation routine of step S7 is executed as it stands, there is a danger that it will not be possible to accurately evaluate the "wall thinning".

Therein, in the embodiment, by extracting the potential difference data Vi in the energizing direction from among all the potential difference data Vi taken, arranging the potential difference data Vi in the energizing direction in order of increasing value, and calculating an average potential difference, which is an average value of a predetermined number of items of potential difference data Vi from an item with the smallest value, it is possible, eliminating potential difference data Vi which have been affected by damage due to a "crack", to identify the amount of wall thinning. As the predetermined number, it being possible to make it appropriate based on a size of a crack commonly occurring in the inspection area R, in a case in which a dimension of a crack is small in comparison with a size of the inspection area R, it is sufficient that it is around half of the number of items of potential difference data Vi in the energizing direction.

Then, in the "wall thinning" evaluation routine of step S10, in the analysis section 40, a logical value of potential difference data assumed when the thickness of the specimen B is taken to be the parameter t is calculated from the resistivity of the specimen B, the dimension of the intervals between the probes which take the potential difference data Vi, and the current value of the current sent through the inspection area R by the energizing section 10, and the hypothetical damage parameter t which represents the thickness of the specimen B is identified, in the same way as in step S7, using the logical value and the average potential difference.

Then, in the analysis section 40, the amount of wall thinning is identified from a difference between the acquired thickness parameter t of the specimen B and the original thickness dimension of the specimen B (step S11).

Meanwhile, in step S9, in the event that the number of items of potential difference data Vi for which the difference between the reference data H and the potential difference data Vi is equal to or greater than the predetermined threshold value is less than or equal to the predetermined number, and in the event that the amount of wall thinning is identified in step S11, the analysis section 40 executes a "crack" evaluation routine (step S12), identifying a crack shape.

Figure 3:
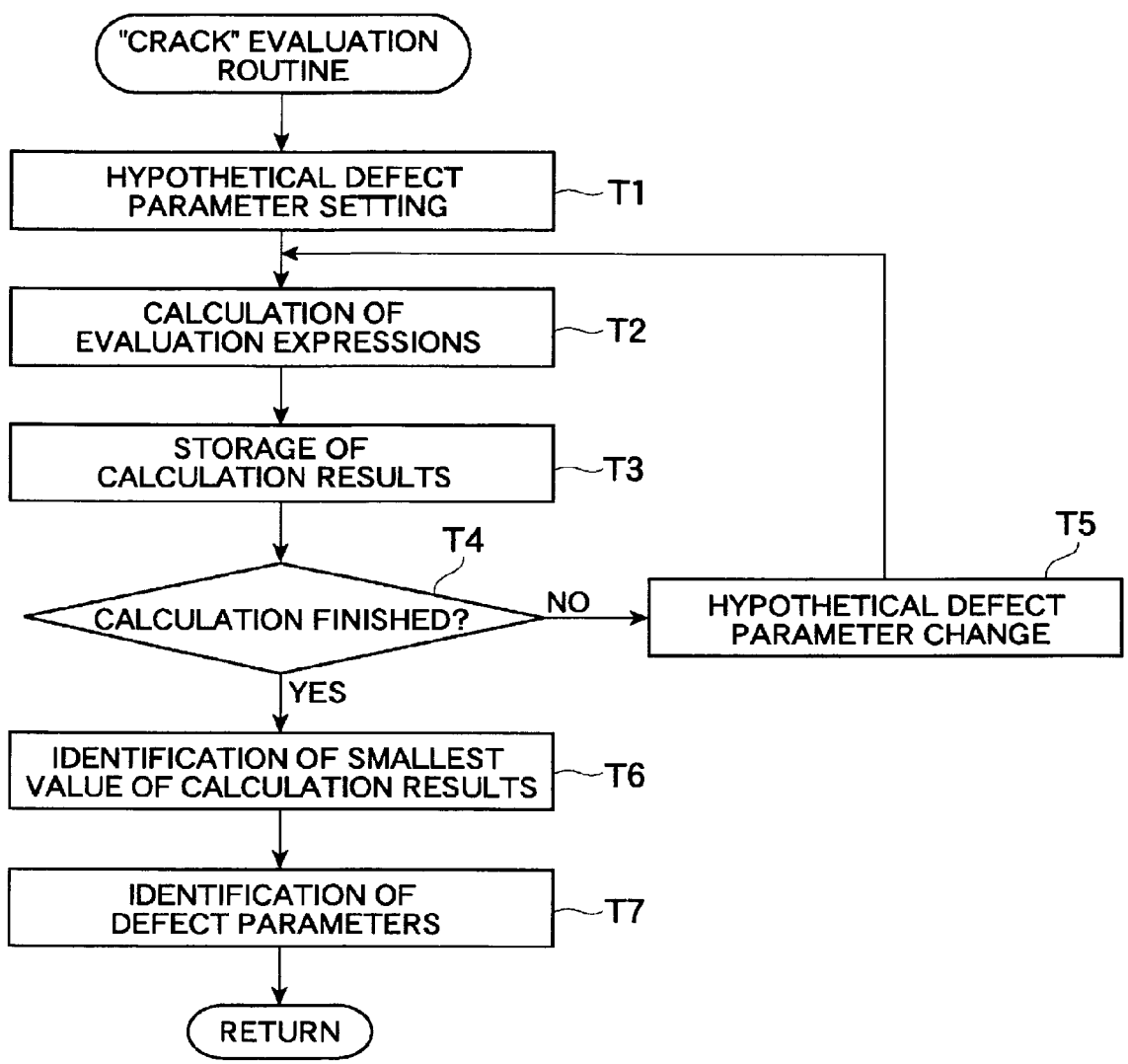
FIG. 3 is a flowchart of a "crack" evaluation routine.

In the "crack" evaluation routine, the analysis section 40 executes a process based on the flowchart shown in FIG. 3, carrying out an identification of the "crack".

Figure 4:
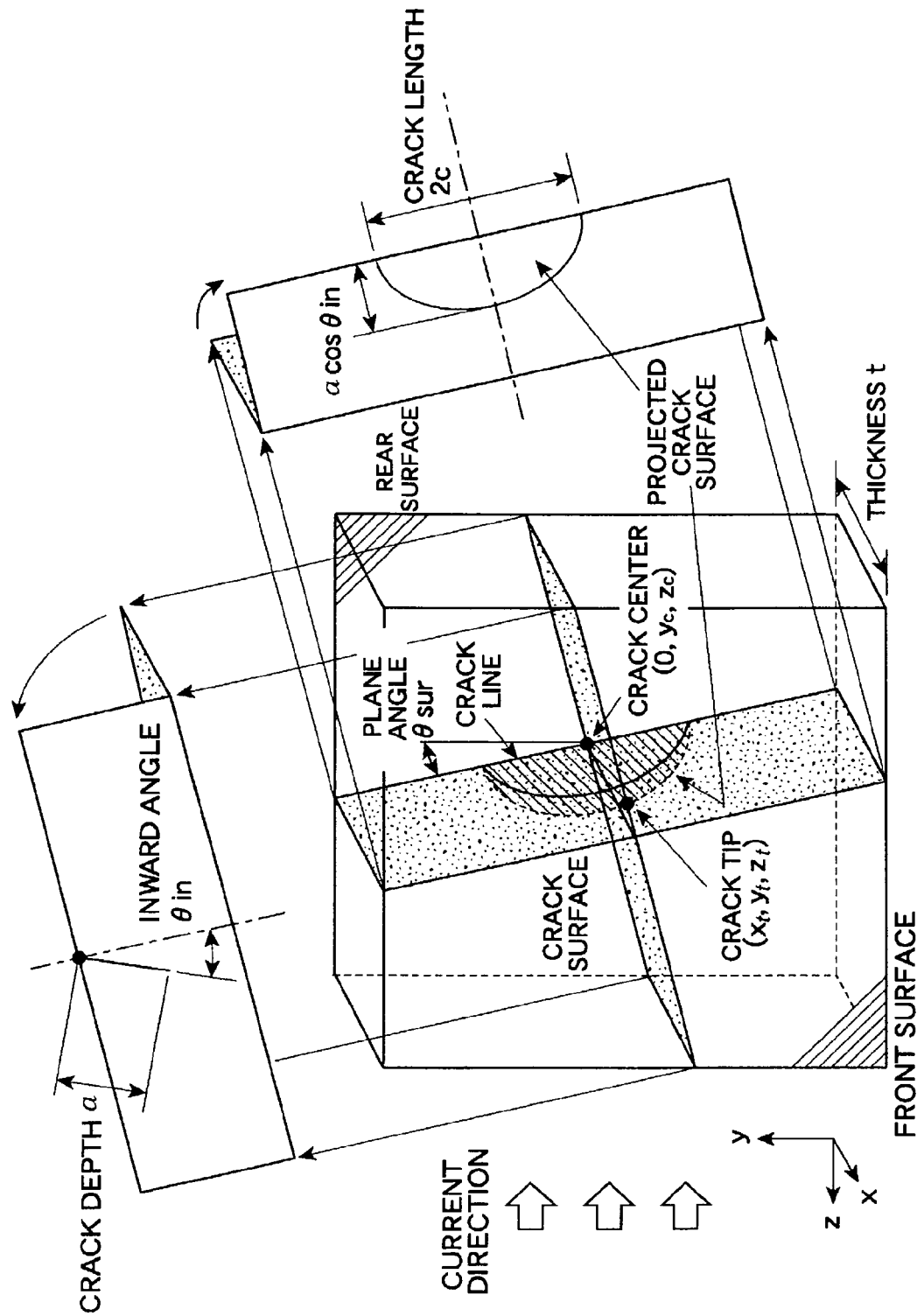
FIG. 4 is an illustration of parameters of a hypothetical damage.

Firstly, the analysis section 40 sets parameters hypothesizing the shape of the "crack" (step T1). Herein, taking the crack to be formed in a semi-elliptical shape on a rear surface side of the specimen, as shown in FIG. 4, taking a y coordinate of a central position of the crack to be $y_c$, and a z coordinate thereof to be $z_c$, a y coordinate of an extreme position of the crack, which is a position in the crack farthest removed from a surface, to be $y_t$, and a z coordinate thereof to be $z_t$, a surface angle to be $\theta_{sur}$, an inward angle to be $\theta_{in}$, a crack length to be c, and a crack depth to be a, a hypothetical damage is set by the six parameters ($y_c$, $z_c$, c, a, $\theta_{in}$, $\theta_{sur}$).

Herein, $$y_t = y_c + a \cdot \sin\theta_{in} \cdot \sin\theta_{sur}$$

$$z_t = z_c - a \cdot \sin\theta_{in} \cdot \cos\theta_{sur}$$

Next, in the analysis section 40, a calculation is carried out with evaluation expressions for the parameters set in step T1 (step T2).

Herein, the evaluation expressions are set as follows. That is, firstly, using the potential difference data Vi, which are a potential difference V in each probe interval, actually taken and stored in step S2, a normalized potential difference increment is calculated with the following equation (1). The calculation of the potential difference V in the probe intervals being carried out for each adjoining probe pair in the current energizing direction, the calculation of the normalized potential difference increment is also carried out for all of them.

[Equation 1]

$$\frac{\Delta V}{V_0} = \frac{V}{V_0} - 1 \tag{1}$$

Herein, $\Delta V$ being a potential difference increment due to the existence of a damage such as a crack or a wall thinning, $V_0$ is a potential difference in a case in which no damage exists.

Next, as an initial value, the heretofore mentioned combination of the central position of the crack, crack length, crack depth and crack plane angle ($y_c$, $z_c$, c, a, $\theta_{in}$, $\theta_{sur}$) is set, a calculation of a potential in each probe position is carried out using a defect-current modification method, and a normalized potential difference increment $\Delta V/V_0$ between each pair of probes is obtained from the calculated potentials with the following equation (2).

[Equation 2]

$$\frac{\Delta V}{V_0} = \frac{|\phi_{E1} - \phi_{E2}|}{|Z_1 - Z_2| \cdot c \cdot E_\infty} - 1 \tag{2}$$

Herein, $\phi_{E1}$ and $\phi_{E2}$ being potentials at two probe positions which configure that pair of probes, and $Z_1$ and $Z_2$ being z coordinates of probe positions normalized by the crack length c, $E_\infty$ is a strength of a remote electric field. This calculation too is carried out for each adjoining probe pair in the current energizing direction.

Then, in order to compare the actual potential difference between probes measurement values and the values of the potential difference between probes calculated for the hypothesized ($y_c$, $z_c$, c, a, $\theta_{in}$, $\theta_{sur}$), an error $E_R$, obtained with the following equation (3), is obtained.

[Equation 3]

$$E_R = \sum_{j=1}^n \left[ \left\{\left(\frac{\Delta V}{V_0}\right)_{C+}\right\}_j - \left\{\left(\frac{\Delta V}{V_0}\right)_{M+}\right\}_j \right] (j = 1, 2, 3, \ldots, n) \tag{3}$$

Herein, the equations inside the large brackets in Equation (3) being respectively a value calculated for each potential difference between probes (a probe pair number j), and a measurement value corresponding thereto, in the event that a value is negative, a conversion replacing it with 0 is performed for both values in parentheses.

With the error $E_R$ of Equation (3) as an evaluation expression, a calculation is carried out with the evaluation expression in the analysis section 40 (step T2).

Figure 5A:
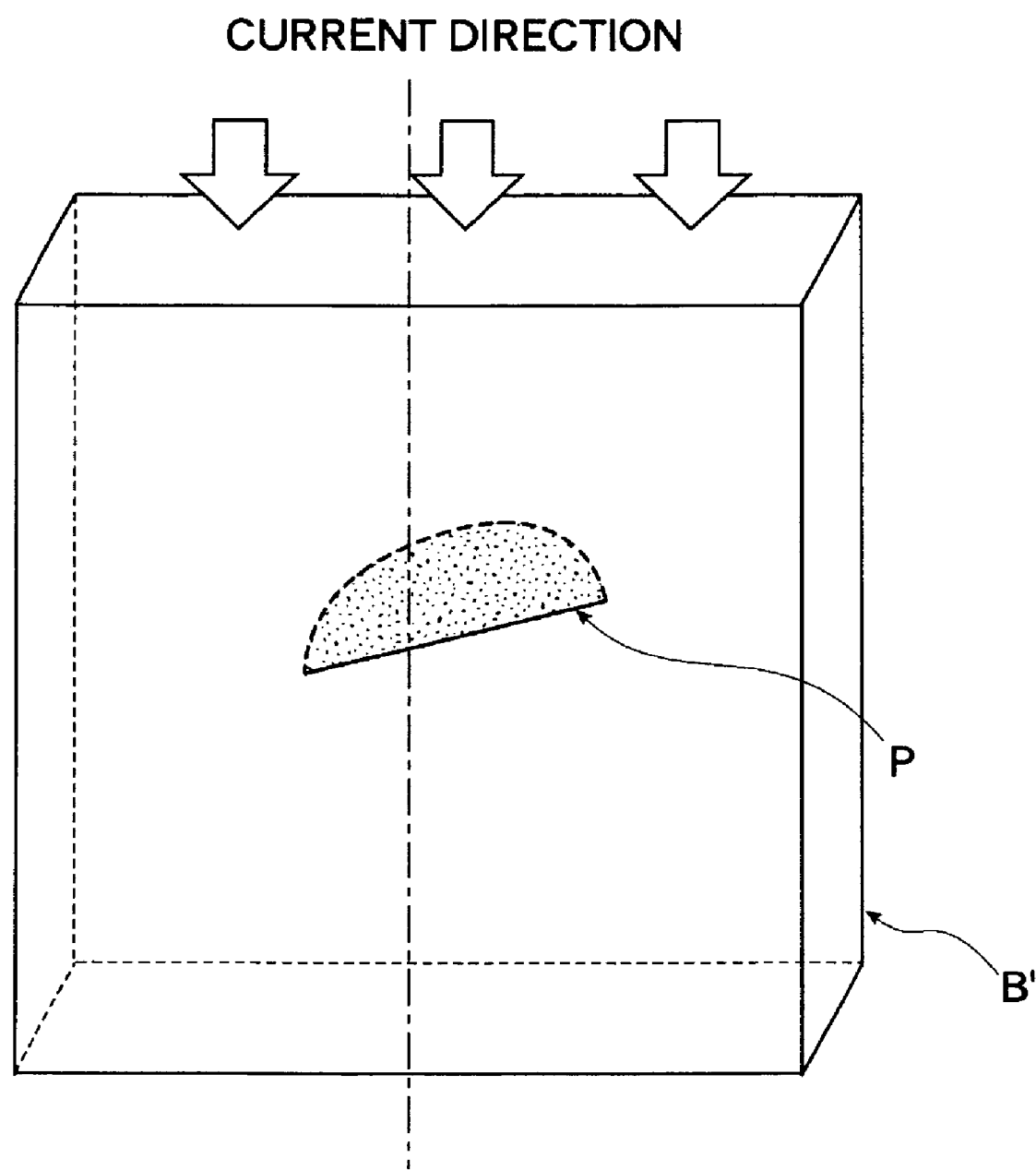
Figure 5B:
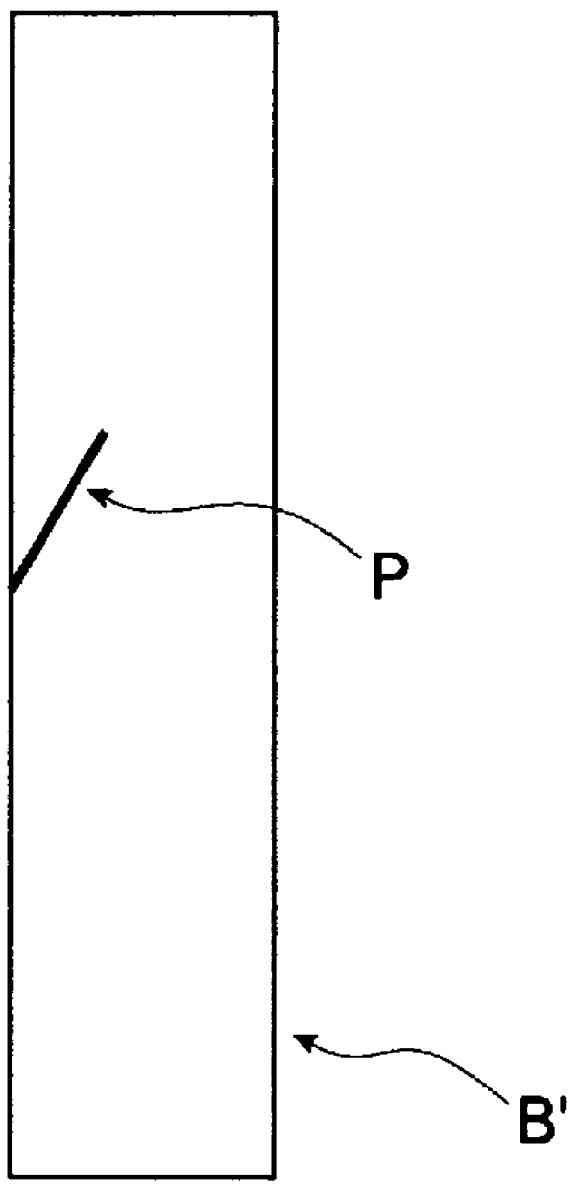
FIG. 5B is an illustration of a crack in an x-z plane of FIG. 5A when $y=y_c$.
Figure 6A:
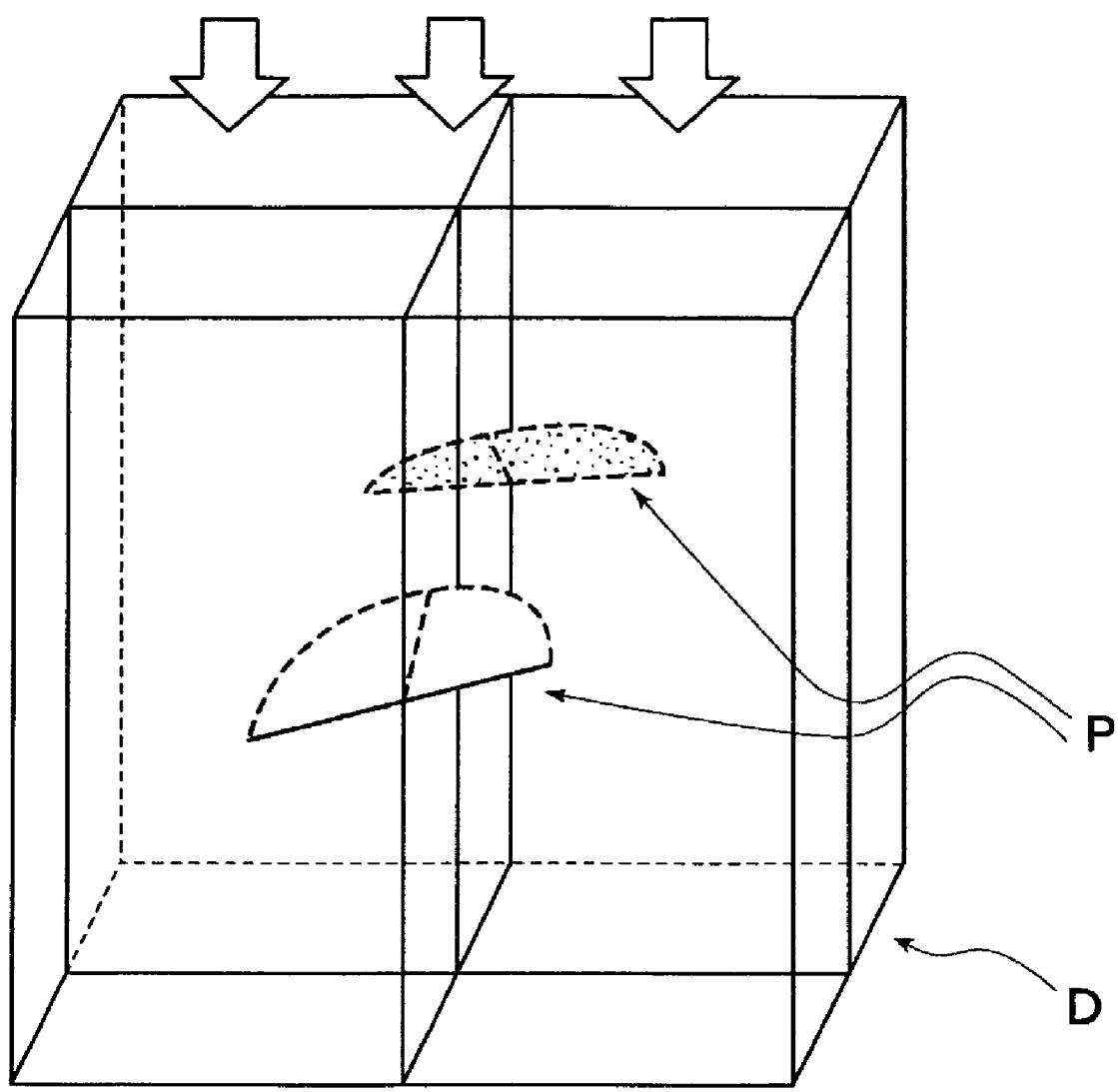
Figure 6B:
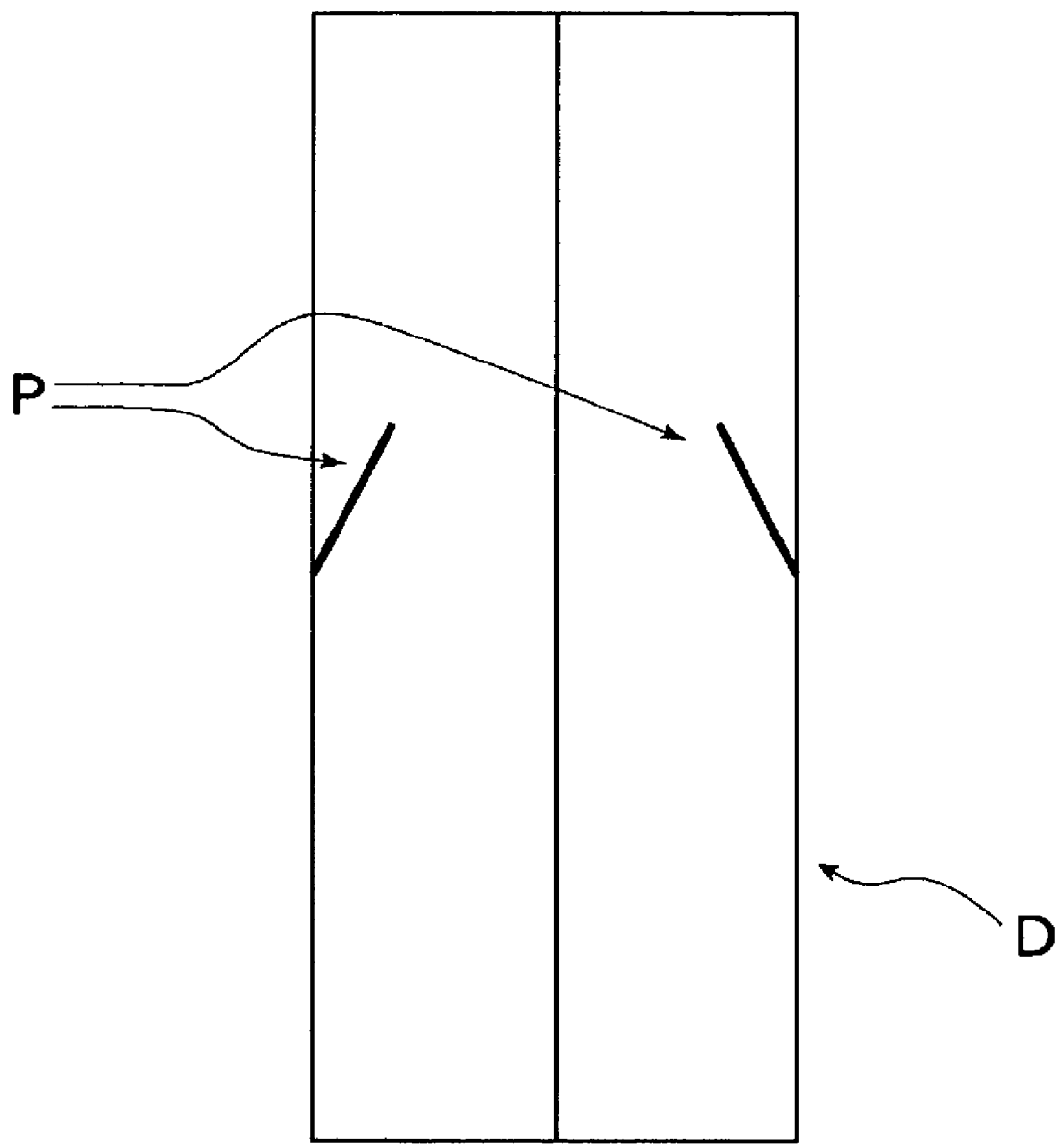
FIG. 6B is an illustration of a crack in an x-z plane of FIG. 6A when $y=y_c$.

In particular, with the calculation with the evaluation expression, in the invention, a double body D is set in which specimens B', on rear surface sides of which cracks P are formed in a semi-elliptical shape, assumed as shown in FIG. 5A, are doubled by bringing them together at their front surfaces, as shown in FIG. 6A. Herein, FIG. 5B showing the crack P in an x-z plane when y=0, FIG. 6B shows an x-z plane of the double body D when y=0.

Figure 7A:
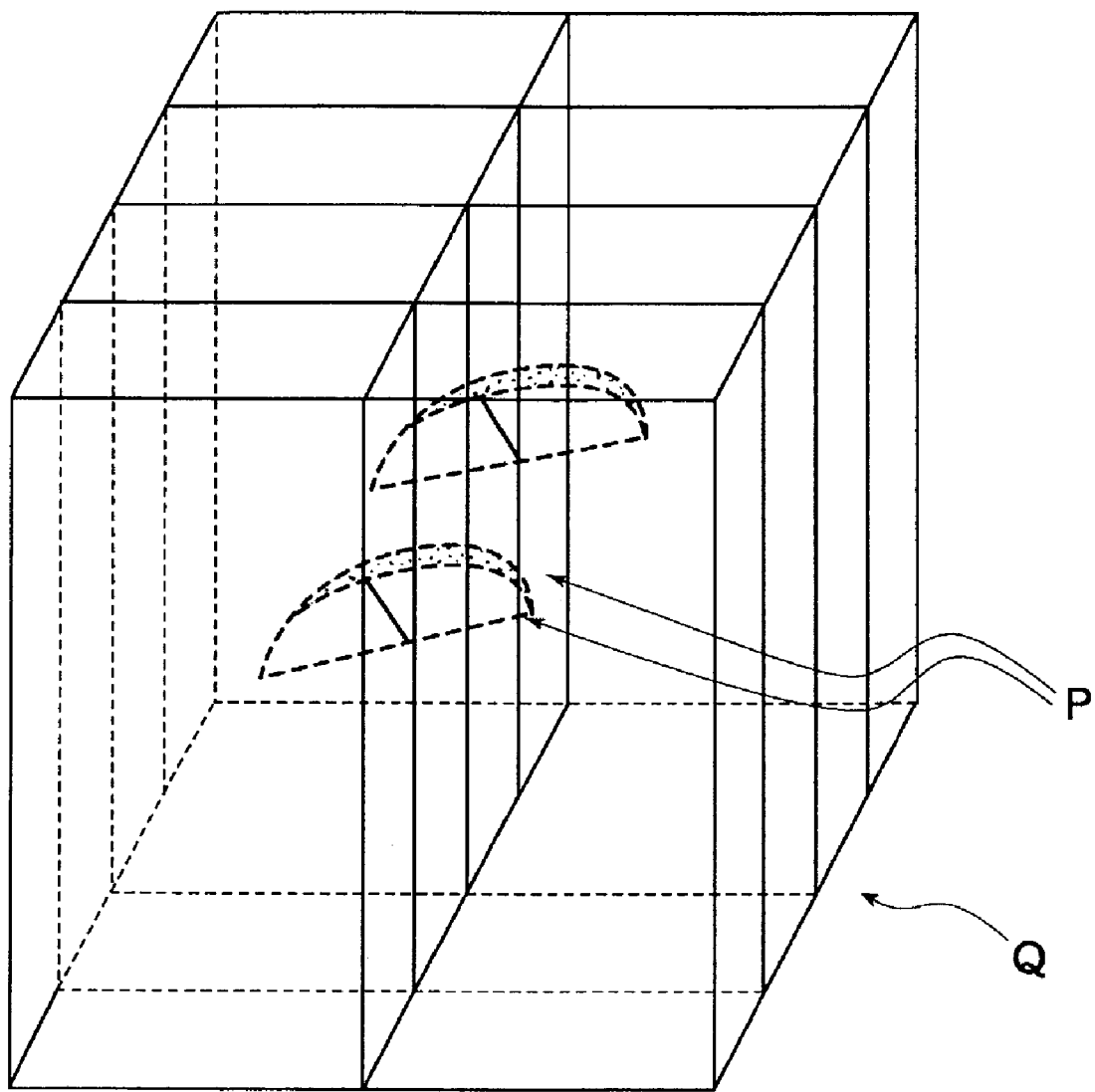

Then, furthermore, as shown in FIG. 7A, a quadruple body Q is set, quadrupled by bringing a rear surface of a specimen B' together with a rear surface of each specimen B' in the double body D. Herein, FIG. 7B shows an x-z plane of the quadruple body Q when y=0.

Figure 7B:
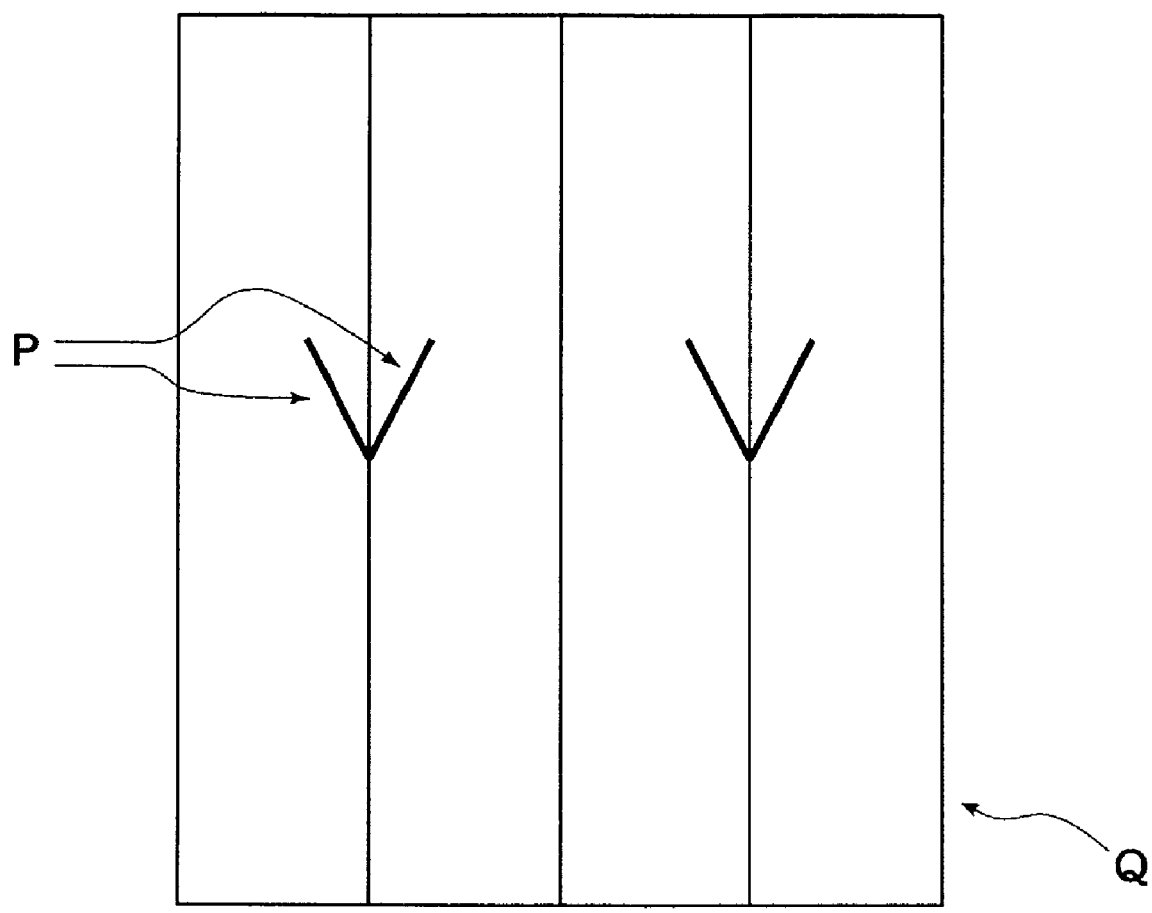
FIG. 7B is an illustration of a crack in an x-z plane of FIG. 7A when $y=y_c$.
Figure 8A:
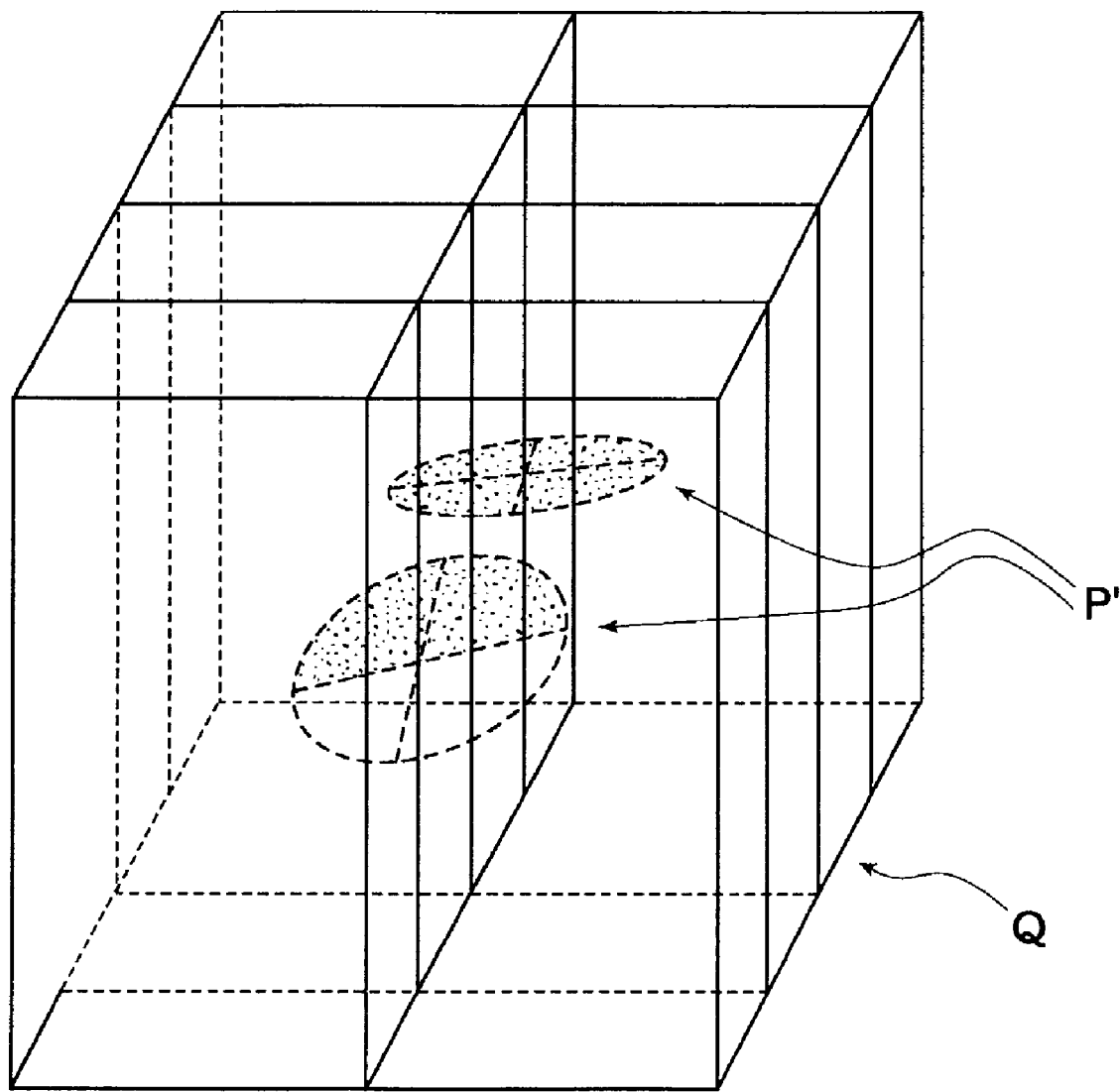
Figure 8B:
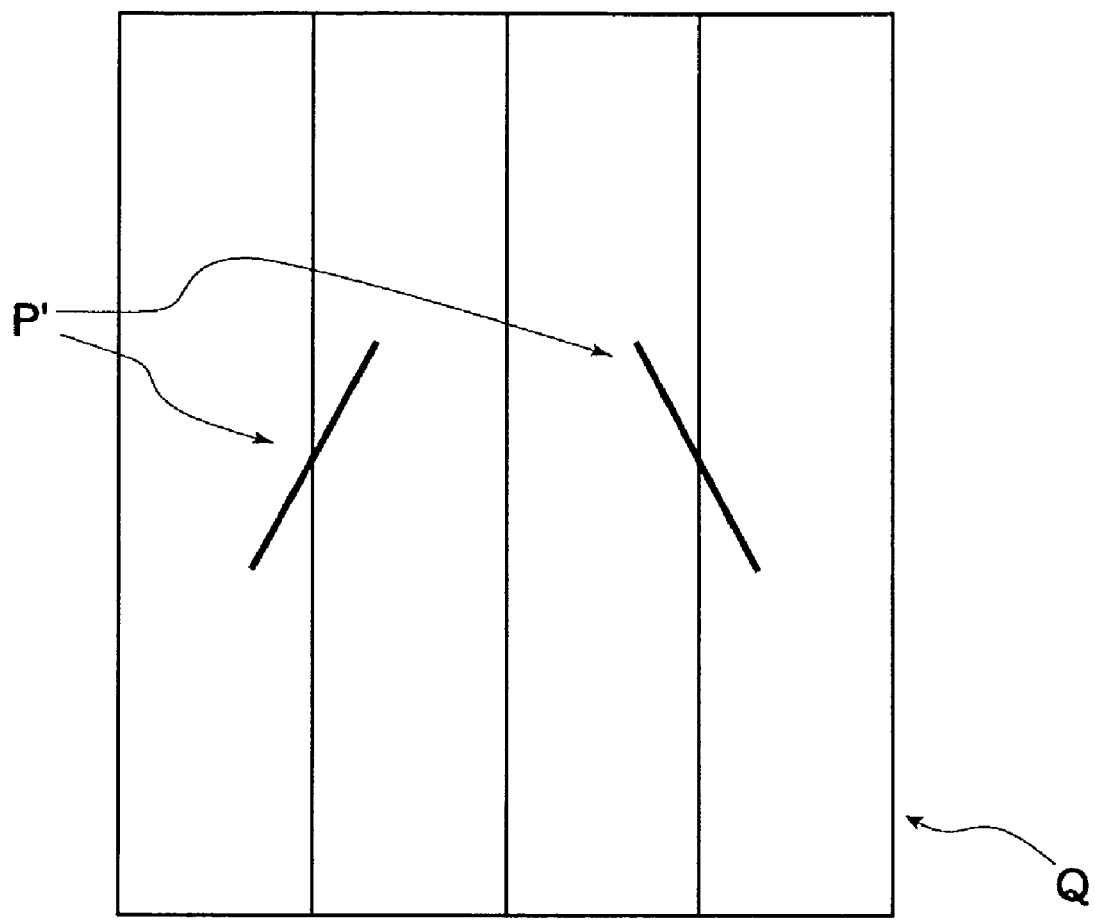
FIG. 8B is an illustration of a crack in an x-z plane of FIG. 8A when $y=y_c$.

Then, as shown in FIG. 7B, in this case, the crack P is V-shaped but, as a result of a calculation is the same even when causing the crack on one side to continue on from the crack on the other side, a calculation is carried out taking an elliptical crack P' to be formed by causing the crack on one side to continue on from the crack on the other side, as shown in FIG. 8A and FIG. 8B.

By using the quadruple body Q in this way, it is possible, avoiding a boundary value problem on a surface portion of the specimen B', to achieve a simplification of the calculation, and moreover, as two mutually plane-symmetrical elliptical cracks P' are formed in the quadruple body Q, it being possible to achieve a simplification of the calculation by utilizing this symmetry, it is possible to perform the calculation in a still shorter time.

Using the quadruple body Q having the elliptical cracks P', in the analysis section 40, the calculation with the evaluation expression of Equation (3) is carried out, and a calculation result is stored in a storage device (step T3).

Subsequently, the analysis section 40 carries out a calculation finishing determination (step T4). That is, the analysis section 40 determines whether all of the values of the parameters, consisting of ($y_c$, $z_c$, c, a, $\theta_{in}$, $\theta_{sur}$), indicating the hypothetical damage have been calculated and, in the event that there is a parameter value which has not been calculated, changes the parameters of the hypothetical damage (step T5), returns to step T2, and carries out the calculation with the evaluation expression based on the changed parameters.

In the event that all of the values of the parameters have been calculated in step T4, the analysis section 40 extracts from among the calculation results a smallest value of the error $E_R$, which is the evaluation expression (step T6), identifies values of parameters which form the error $E_R$ as maximum likelihood estimation values (step T7), and finishes the "crack" evaluation routine.

In the analysis section 40, the shape of the "crack" is identified from the parameters identifying the shape of the "crack" acquired in the "crack" evaluation routine (step S13) and, in step S6, the crack shape identified in step S13, and the amount of wall thinning in the event that a wall thinning is occurring, are output.

In this way, by evaluating the "crack" and the "wall thinning" separately, it is possible to increase a processing speed in the analysis section 40.

Also, rather than evaluating the "crack" and the "wall thinning" separately, it is possible to simultaneously evaluate a "crack opening" and the "wall thinning" by, in addition to the "crack" hypothetical damage parameters ($y_c$, $z_c$, c, a, $\theta_{in}$, $\theta_{sur}$), assuming eight parameters ($y_c$, $z_c$, c, a, $\theta_{in}$, $\theta_{sur}$, b, t), a parameter b representing an opening of the "crack" and the parameter t representing the thickness of the specimen B being added, and carrying out a calculation using the maximum likelihood estimation method.

Furthermore, by carrying out a calculation of the parameter t representing the thickness of the specimen B as a variable over the inspection area R, it is also possible to evaluate a non-uniform "wall thinning".

Example

Figure 9:
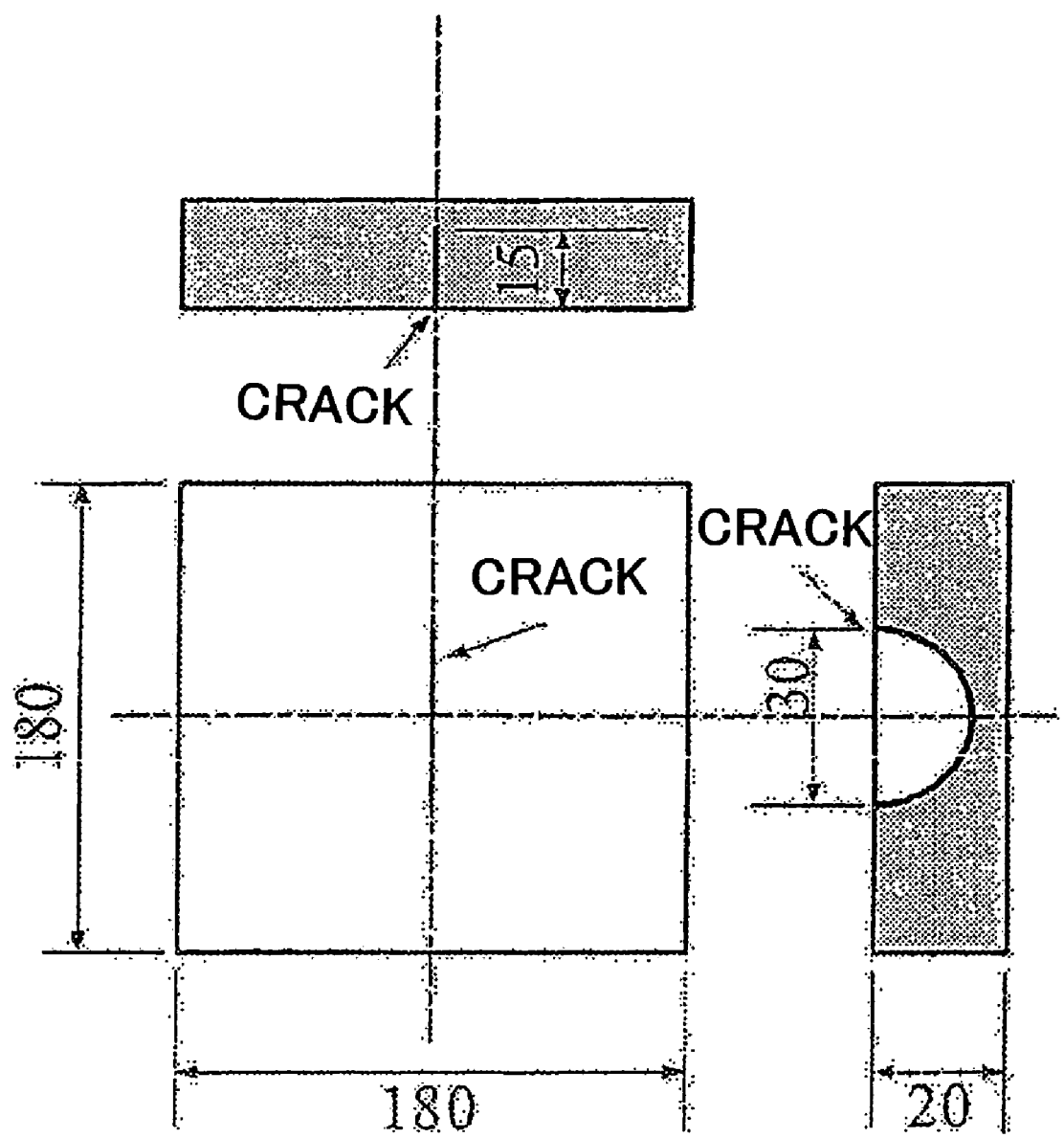
FIG. 9 is an illustration of a test specimen 1.
Figure 10:
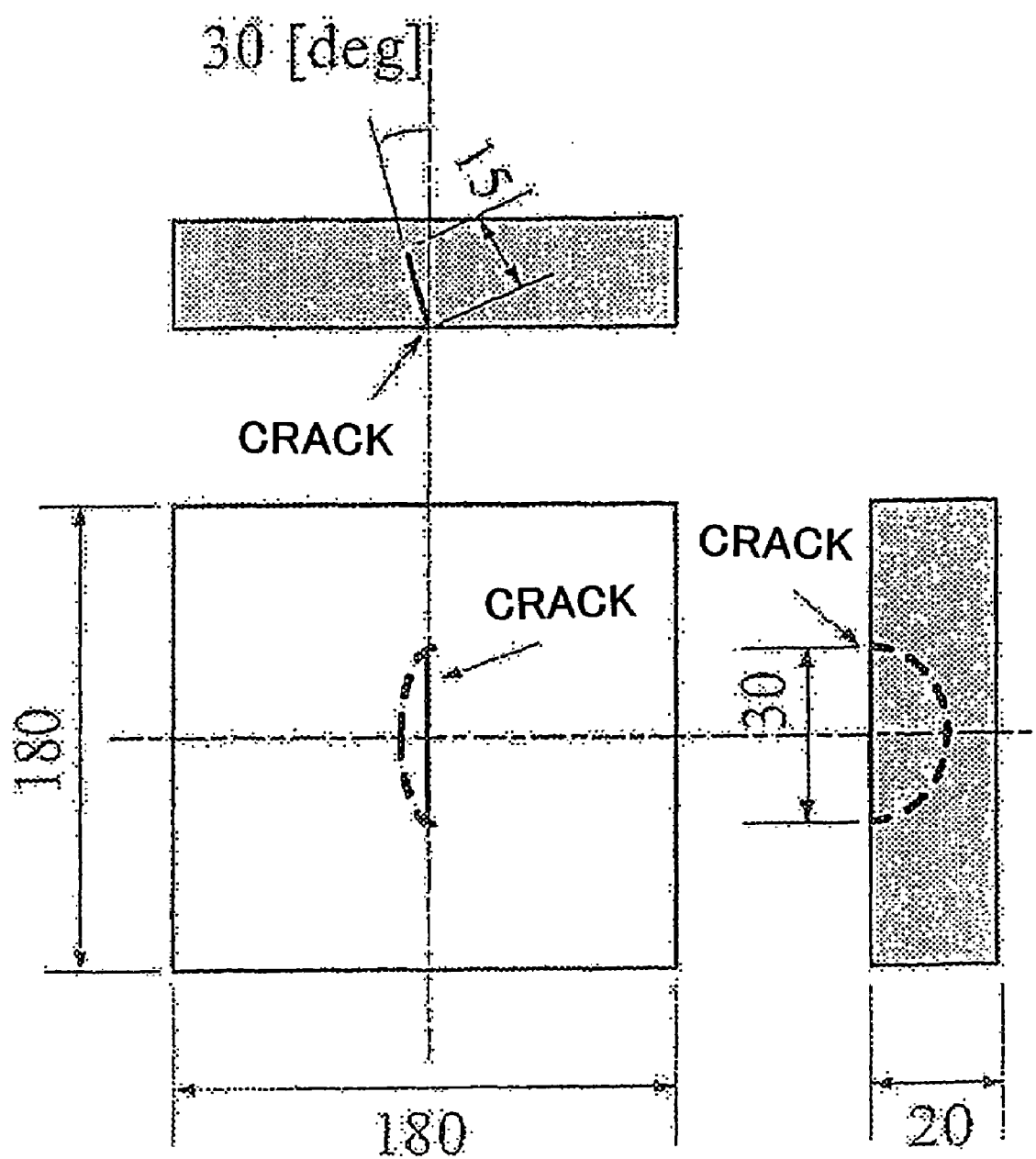
FIG. 10 is an illustration of a test specimen 2.
Figure 11:
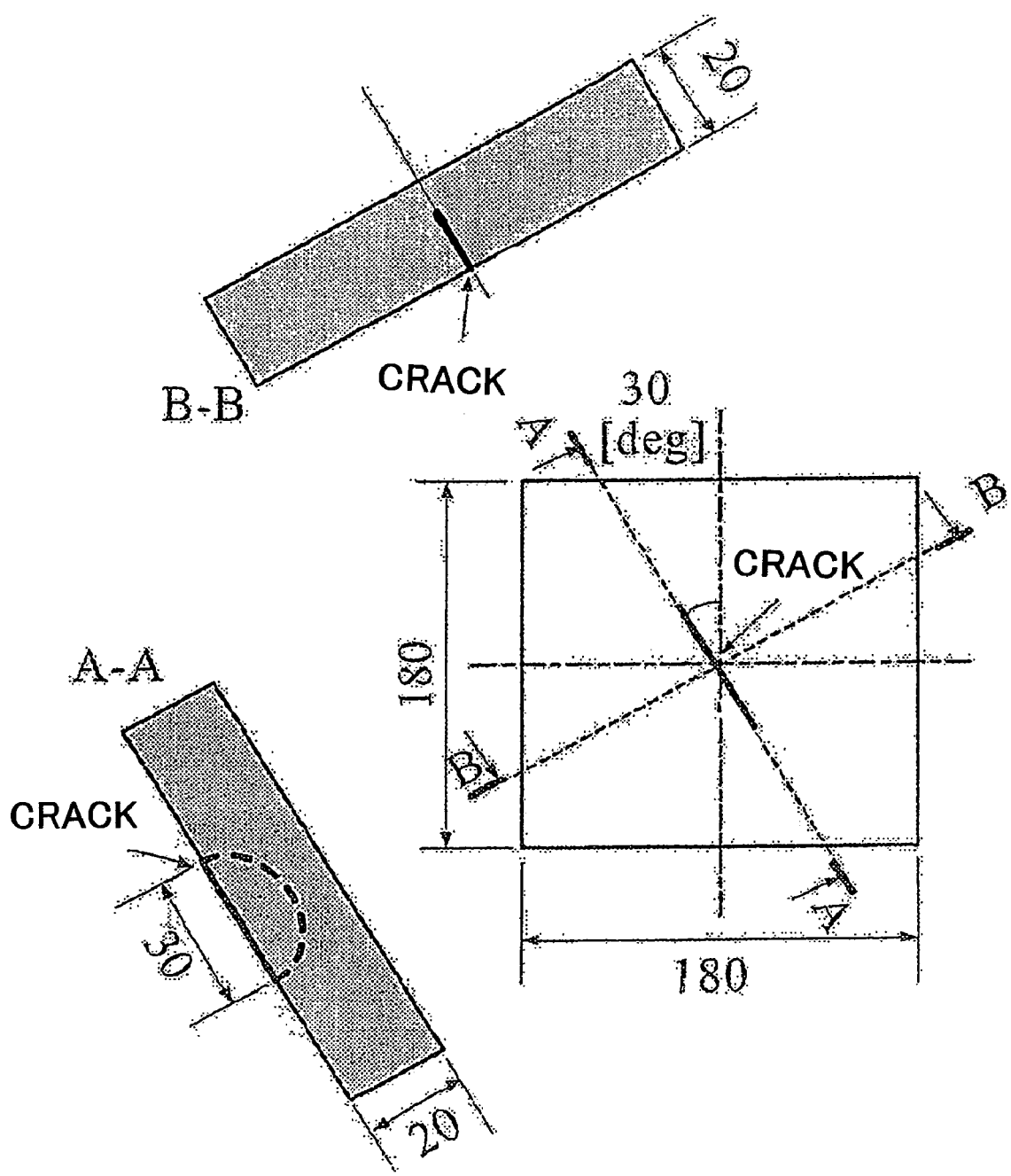
FIG. 11 is an illustration of a test specimen 3.

Test specimens 1 to 3 are compiled by preparing austenitic stainless steel (SUS304) 180 mm×180 mm×20 mm flat test specimens, and introducing a semi-circular crack, of which an overall length 2c=30 mm and a depth a=15 mm, into each of the flat test specimens by means of an electrical discharge, as shown in FIGS. 9 to 11.

The test specimen 1 is given a surface angle $\theta_{sur}$ of 0 degrees, and an inward angle $\theta_{in}$ of 0 degrees. The test specimen 2 is given a surface angle $\theta_{sur}$ of 0 degrees, and an inward angle $\theta_{in}$ of 30 degrees. The test specimen 3 is given a surface angle $\theta_{sur}$ of 30 degrees, and an inward angle $\theta_{in}$ of 0 degrees.

Figure 12:
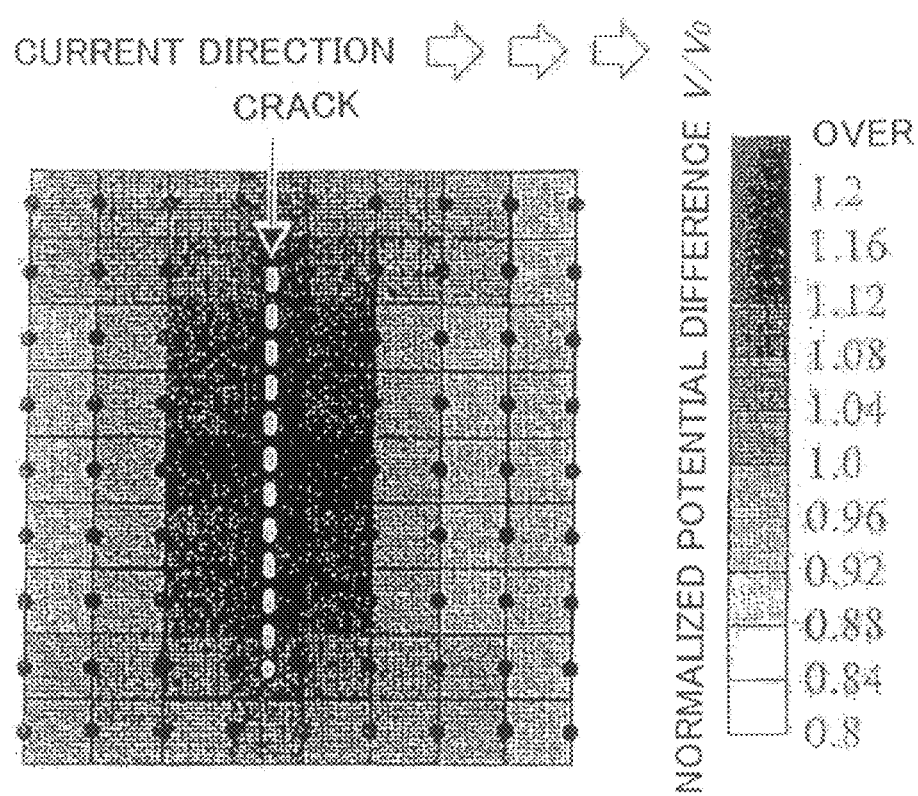
FIG. 12 is a distribution chart of normalized potential difference $V/V_0$ in test specimen 1 measurement results.
Figure 13:
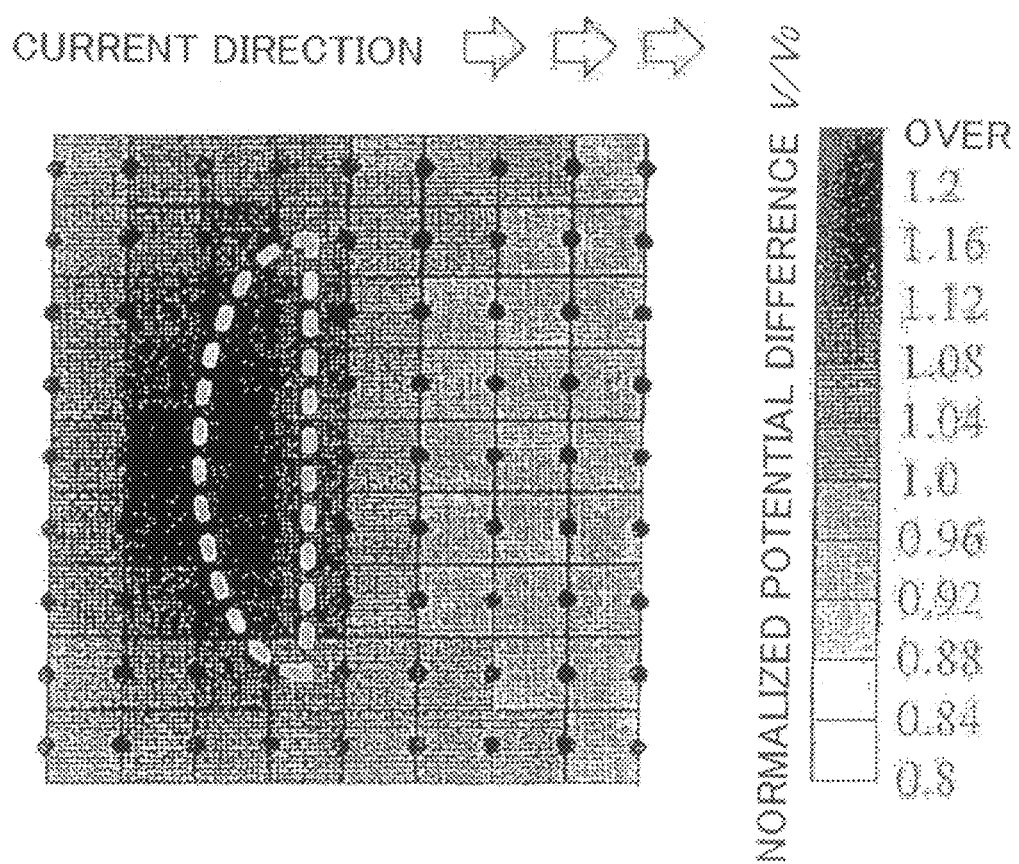
FIG. 13 is a distribution chart of normalized potential difference $V/V_0$ in test specimen 2 measurement results.

An 8 A current is sent through the test specimens 1 to 3 with a Takasago Seisakujo Co., Ltd. constant current direct current power supply device NL08-30 and, with a steel needle as a probe, a potential difference between probes is measured in predetermined positions using an Advantest Co., Ltd. digital multimeter R6561. The measurement of the potential difference between probes is carried out by assuming grid-like rectangular areas in which a surface of the test specimen is divided into eight, at 5 mm intervals, in a current energizing direction, and into nine, at 5 mm intervals, in a direction perpendicular to the current energizing direction, and measuring the potential difference in each rectangular area. Of course, the measurement of the potential difference between probes is carried out on a rear side of a surface into which the semi-circular crack has been introduced. A distribution of a normalized potential difference $V/V_0$ of test specimen 1 measurement results is shown in FIG. 12. A distribution of a normalized potential difference $V/V_0$ of test specimen 2 measurement results is shown in FIG. 13. A distribution of a normalized potential difference $V/V_0$ of test specimen 3 measurement results is shown in FIG. 14.

Figure 14:
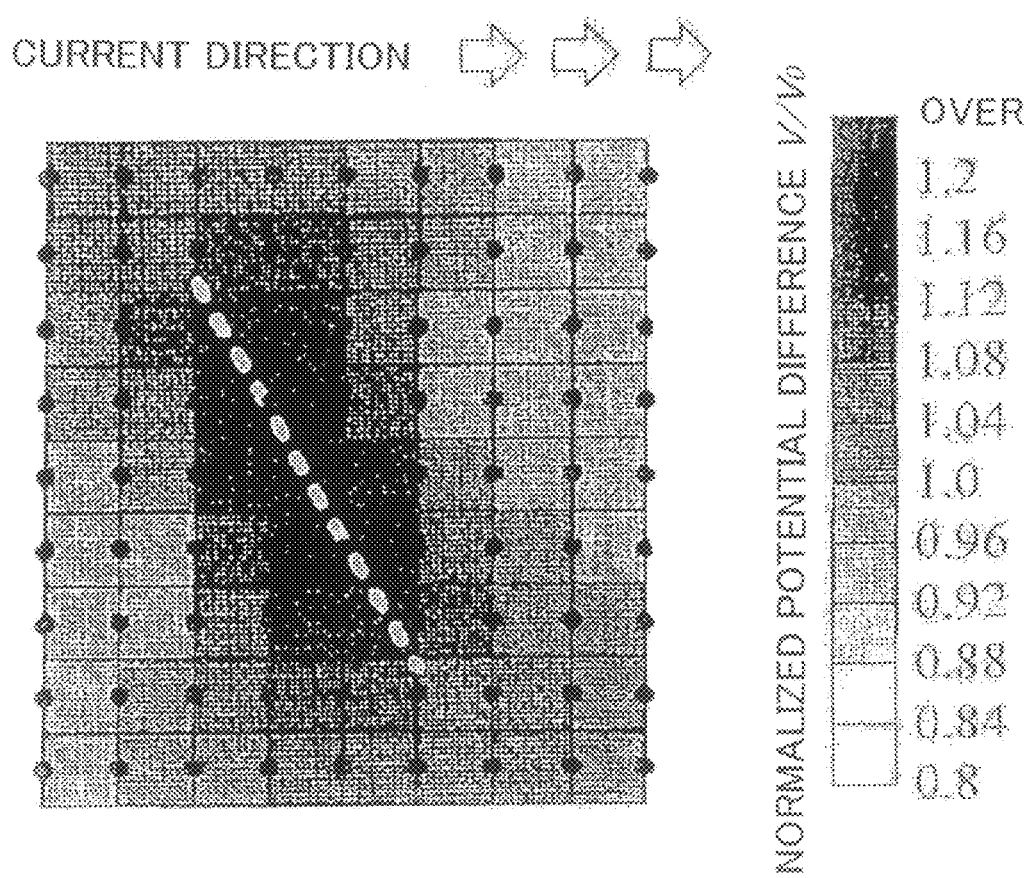
FIG. 14 is a distribution chart of normalized potential difference $V/V_0$ in test specimen 3 measurement results.

As is clear from FIGS. 12 to 14, it can be understood that a value of the normalized potential difference changes due to the existence of a crack. Also, it can be understood that in the event that when the crack plane angle differs, the potential difference distribution on the rear surface changes accordingly.

Results of carrying out detections of the crack shapes for the test specimens 1 to 3 are shown in the table below. As shown in the table below, it can be understood that, with respect to an actual crack shape, the crack can be detected with extreme precision. (a) in the table below is the case of the test specimen 1, (b) in the table below is the case of the test specimen 2, and (c) in the table below is the case of the test specimen 3.

TABLE 1

| Condition | Surface angle $\theta_{sur}$ (deg) | | Depth angle $\theta_{in}$ (deg) | | Length c (mm) | | Depth a (mm) | | Horizontal position $y_c$ (mm) | | Vertical position $z_c$ (mm) | |
|---|---|---|---|---|---|---|---|---|---|---|---|---|
| | Actual | Estimate | Actual | Estimate | Actual | Estimate | Actual | Estimate | Actual | Estimate | Actual | Estimate |
| (a) | 0 | 0 | 0 | 0 | 15.0 | 15.0 | 15.0 | 14.0 | 22.5 | 22.5 | 22.5 | 22.5 |
| (b) | 0 | 0 | 30 | 27 | 15.0 | 16.0 | 15.0 | 13.0 | 22.5 | 22.5 | 22.5 | 22.5 |
| (c) | 30 | 30 | 0 | 0 | 15.0 | 16.0 | 15.0 | 13.5 | 22.5 | 22.5 | 22.5 | 22.5 |

INDUSTRIAL APPLICABILITY

In this way, the damage detection apparatus and damage detection method of the invention can accurately detect a damage such as a crack or a wall thinning occurring in a specimen, and moreover, it being possible to detect almost always accurately, and in an extremely short time, even from a rear surface side, it is possible to carry out an inspection of various kinds of structure, including an inspection of piping in a power plant or chemical plant, highly efficiently and at a low cost.

The invention claimed is:

1. A damage detection apparatus which detects a damage occurring in a specimen, which is a subject of detection, the apparatus comprising:
   energizing means which energizes in order to put an inspection area on the specimen into a predetermined energized condition;
   potential difference measurement means which measures a potential difference at predetermined intervals in the inspection area;
   storage means which stores a plurality of items of potential difference data acquired with the potential difference measurement means; and
   analysis means which analyses an existence or otherwise of a damage, and a shape thereof, based on the potential difference data stored in the storage means, wherein
   the analysis means:
      sets parameters specifying a hypothetical damage,
      sets the hypothetical damage by six parameters ($y_c$, $z_c$, c, a, $\theta_{in}$, $\theta_{sur}$) so as to satisfy the following equation $$y_t = y_c + a \cdot \sin\theta_{in} \cdot \sin\theta_{sur}, \quad z_t = z_c - a \cdot \sin\theta_{in} \cdot \cos\theta_{sur},$$

herein, $y_c$ is a y coordinate of a central position of the hypothetical damage, $z_c$ is a z coordinate thereof, $y_t$ is a y coordinate of an extreme position of the hypothetical damage, which is a position in the crack farthest from a surface, $z_t$ is a z coordinate thereof, $\theta_{sur}$ is a surface angle, $\theta_{in}$ is an inward angle, c is a crack length, and a is a hypothetical damage depth, and
      sets hypothetical specimens having the hypothetical damage on a rear surface side and, forms a double body by bringing together front surfaces of the hypothetical specimens, forms a quadruple body by further bringing rear surfaces of the hypothetical specimens together with rear surfaces of the respective hypothetical specimens which form the double body, estimates that the hypothetical damage is formed on the quadruple body by causing the hypothetical damage formed on the rear surfaces of the respective hypothetical specimens which constitute the double body and the hypothetical damage formed on the rear surfaces of the respective hypothetical specimens in forming the quadruple body to continue, and calculates a potential at respective terminal positions for measuring the potential difference based on the parameters, and
      calculates a normalized potential difference increment $\Delta V/V_0$ between each pair of probes with the following equation, $$\frac{\Delta V}{V_0} = \frac{|\phi_{E1} - \phi_{E2}|}{|Z_1 - Z_2| \cdot c \cdot E_\infty} - 1$$

herein, $\phi_{E1}$ and $\phi_{E2}$ being potentials at two probe positions which configure that pair of probes, and $z_1$ and $z_2$ being z coordinates of probe positions normalized by the crack length c, $E_\infty$ being a strength of a remote electric field, $\Delta V$ being a potential difference increment due to the existence of the damage, and $V_0$ being a potential difference in a case in which no damage exists, and
      executes a following evaluation formula by changing the parameters using a maximum likelihood estimation method thus calculating a maximum likelihood estimation value, $$E_R = \sum_{j=1}^{n} \left[\left\{\left(\frac{\Delta V}{V_0}\right)_{c+}\right\}_j - \left\{\left(\frac{\Delta V}{V_0}\right)_{M+}\right\}_j\right] (j = 1, 2, 3, \ldots, n)$$

herein, $(\Delta V/V_0)_{c+}$ being a calculated value, $(\Delta V/V_0)_{M+}$ being a measured value and j being a probe pair number, and
      detects an existence or otherwise of a damage and/or a shape of the damage from the maximum likelihood estimation value.

2. The damage detection apparatus according to claim 1, wherein
   in the event that the damage is a crack formed in the specimen,
   the analysis means, when setting the quadruple body having the hypothetical damage, makes the hypothetical damage an elliptical crack.

3. The damage detection apparatus according to claim 1, wherein
   in the event that the damage is a wall thinning of the specimen,
   the analysis means makes a parameter specifying the hypothetical damage a thickness of the specimen, and calculates an amount of wall thinning from a thickness of the specimen calculated by a calculation using the maximum likelihood estimation method.

4. A damage detection method which detects a damage occurring in a specimen, which is a subject of detection, the method comprising:
   a step of, while carrying out a predetermined energizing in an inspection area on the specimen, measuring a plurality of potential differences at predetermined intervals in the inspection area;
   a step of setting the hypothetical damage by the six parameters ($y_c$, $z_c$, c, a, $\theta_{in}$, $\theta_{sur}$) so as to satisfy the following equation $$y_t = y_c + a \cdot \sin\theta_{in} \cdot \sin\theta_{sur}, \quad z_t = z_c - a \cdot \sin\theta_{in} \cdot \cos\theta_{sur},$$

herein is a coordinate of a central position of the hypothetical damage, $z_c$ is a z coordinate thereof, $y_t$ is a y coordinate of an extreme position of the hypothetical damage, which is a position in the crack farthest from a surface, $z_t$ is a z coordinate thereof, $\theta_{sur}$ is a surface angle, $\theta_{in}$ is an inward angle, c is a crack length, and a is a hypothetical damage depth;
   a step of setting hypothetical specimens having the hypothetical damage on a rear surface side and, forming a double body by bringing together front surfaces of the hypothetical specimens, forming a quadruple body by further bringing rear surfaces of the hypothetical specimens together with rear surfaces of the respective hypothetical specimens which form the double body, estimating that the hypothetical damage is formed on the quadruple body by causing the hypothetical damage formed on the rear surfaces of the respective hypothetical specimens which constitute the double body and the hypothetical damage formed on the rear surfaces of the respective hypothetical specimens in forming the quadruple body to continue, and calculating a potential at respective terminal positions for measuring the potential difference based on the parameters, and a step of calculating a normalized potential difference increment $\Delta V/V_0$ between each pair of probes is obtained with the following equation, $$\frac{\Delta V}{V_0} = \frac{|\phi_{E1} - \phi_{E2}|}{|Z_1 - Z_2| \cdot c \cdot E_\infty} - 1$$

herein, $\Phi_{E1}$ and $\Phi_{E2}$ being potentials at two probe positions which configure that pair of probes, and $z_1$ and $z_2$ being z coordinates of probe positions normalized by the crack length c, $E_\infty$ is a strength of a remote electric field, $\Delta V$ being a potential difference increment due to the existence of the damage, and $V_0$ being a potential difference in a case in which no damage exists, and a step of executing the following evaluation formula by changing the parameters using a maximum likelihood estimation method thus calculating a maximum likelihood estimation value, $$E_R = \sum_{j=1}^{n} \left[ \left\{ \left(\frac{\Delta V}{V_0}\right)_{c+} \right\}_j - \left\{ \left(\frac{\Delta V}{V_0}\right)_{M+} \right\}_j \right] (j = 1, 2, 3, \ldots, n)$$

herein, $(\Delta V/V_0)_{c+}$ being a calculated value, $(\Delta V/V_0)_{M+}$ being a measured value, and j being a probe pair number, and detecting an existence or otherwise of a damage and/or a shape of the damage from the maximum likelihood estimation value.

5. A non-transitory computer readable recording medium containing computer instructions stored therein for causing a computer to perform a damage detection program comprising:

a step of, while carrying out a predetermined energizing in an inspection area on the specimen, measuring a plurality of potential differences at predetermined intervals in the inspection area;

a step of setting the hypothetical damage by the six parameters ($v_c$, $z_c$, c, a, $\theta_{in}$, $\theta_{sur}$) so as to satisfy the following equation $$y_t = y_c + a \cdot \sin\theta_{in} \cdot \sin\theta_{sur}, \quad z_t = z_c - a \cdot \sin\theta_{in} \cdot \cos\theta_{sur},$$

herein, $y_c$ is a y coordinate of a central position of the hypothetical damage, $z_c$ is a z coordinate thereof, $y_t$ is a y coordinate of an extreme position of the hypothetical damage, which is a position in the crack farthest from a surface, $z_t$ is a z coordinate thereof, $\theta_{sur}$ is a surface angle, $\theta_{in}$ is an inward angle, c is a crack length, and a is a hypothetical damage depth;

a step of setting hypothetical specimens having the hypothetical damage on a rear surface side and, forming a double body by bringing together front surfaces of the hypothetical specimens, forming a quadruple body by further bringing rear surfaces of the hypothetical specimens together with rear surfaces of the respective hypothetical specimens which form the double body, estimating that the hypothetical damage is formed on the quadruple body by causing the hypothetical damage formed on the rear surfaces of the respective hypothetical specimens which constitute the double body and the hypothetical damage formed on the rear surfaces of the respective hypothetical specimens in forming the quadruple body to continue, and calculating a potential at respective terminal positions for measuring the potential difference based on the parameters, and a step of calculating a normalized potential difference increment $\Delta V/V_0$ between each pair of probes with the following equation, $$\frac{\Delta V}{V_0} = \frac{|\phi_{E1} - \phi_{E2}|}{|Z_1 - Z_2| \cdot c \cdot E_\infty} - 1$$

herein, $\phi_{E1}$ and $\phi_{E2}$ being potentials at two probe positions which configure that pair of probes, and $z_1$ and $z_2$ being z coordinates of probe positions normalized by the crack length c, $E_\infty$ is a strength of a remote electric field, $\Delta V$ being a potential difference increment due to the existence of the damage, and $V_0$ being a potential difference in a case in which no damage exists, and a step of executing the following evaluation formula by changing the parameters using a maximum likelihood estimation method thus calculating a maximum likelihood estimation value, $$E_R = \sum_{j=1}^{n} \left[ \left\{ \left(\frac{\Delta V}{V_0}\right)_{c+} \right\}_j - \left\{ \left(\frac{\Delta V}{V_0}\right)_{M+} \right\}_j \right] (j = 1, 2, 3, \ldots, n)$$

herein, $(\Delta V/V_0)_{c+}$ being a calculated value $(\Delta V/V_0)_{M+}$ being a measured value, and j being a probe pair number, and detecting an existence or otherwise of a damage and/or a shape of the damage from the maximum likelihood estimation value.

* * * * *